United States Patent
Choi et al.

(10) Patent No.: US 11,696,939 B2
(45) Date of Patent: Jul. 11, 2023

(54) COMPOSITIONS CONTAINING EXOSOME CARRYING NF-κB INHIBITORS AND METHODS OF USING THEREOF

(71) Applicants: ILIAS Biologics Inc, Daejeon (KR); ILIAS Therapeutics, Inc., New York, NY (US)

(72) Inventors: Chulhee Choi, Daejeon (KR); Kyungsun Choi, Daejeon (KR); Ramkumar Menon, Galveston, TX (US)

(73) Assignees: ILIAS Biologics Inc., Daejeon (KR); ILIAS Therapeutics, Inc., New York, NY (US)

( * ) Notice: Subject to any disclaimer, the term of this patent is extended or adjusted under 35 U.S.C. 154(b) by 0 days.

(21) Appl. No.: 17/138,864

(22) Filed: Dec. 30, 2020

(65) Prior Publication Data
US 2021/0275636 A1    Sep. 9, 2021

Related U.S. Application Data

(60) Provisional application No. 63/105,207, filed on Oct. 23, 2020, provisional application No. 62/955,339, filed on Dec. 30, 2019.

(51) Int. Cl.
*A61K 35/12* (2015.01)
*A61K 38/17* (2006.01)
(Continued)

(52) U.S. Cl.
CPC .......... *A61K 38/1738* (2013.01); *A61K 9/127* (2013.01); *A61K 31/137* (2013.01); *A61K 31/405* (2013.01); *A61K 31/4025* (2013.01); *A61K 31/43* (2013.01); *A61K 31/4422* (2013.01); *A61K 31/545* (2013.01);
(Continued)

(58) Field of Classification Search
CPC .......................... A61K 38/1728; A61K 35/12
See application file for complete search history.

(56) References Cited

U.S. PATENT DOCUMENTS

| | | | |
|---|---|---|---|
| 9,012,410 B2 * | 4/2015 | Han | A61K 31/7028 514/23 |
| 2010/0035829 A1 | 2/2010 | Han et al. | |
| 2018/0117117 A1 * | 5/2018 | Choi | C07K 14/70596 |

FOREIGN PATENT DOCUMENTS

| | | | | |
|---|---|---|---|---|
| WO | WO-2005021722 A2 * | 3/2005 | ......... | C07K 14/4703 |
| WO | 2018/062973 A1 | 4/2018 | | |

OTHER PUBLICATIONS

Zhong et al. ('Toll-like 4 receptor/NFkB inflammatory/miR-146a pathway contributes to the ART-correlated preterm birth outcome, Oncotarget, 2016, V7, N45, 72475-72485). (Year: 2016).*

(Continued)

*Primary Examiner* — Benjamin J Packard
(74) *Attorney, Agent, or Firm* — Morgan, Lewis & Bockius LLP

(57) ABSTRACT

The present invention is related to compositions containing extracellular vesicles (exosomes) and methods of using the same for increasing lifespan of fetus, viability of fetus, or viability of newborn, for treating inflammation in uterus and/or fetus, for delaying preterm birth, or for treating a condition related to inflammation in uterus and/or fetus, wherein the extracellular vesicles comprising a nuclear factor kappa beta (NF-κB) inhibitor and a photo-specific binding protein.

21 Claims, 14 Drawing Sheets
Specification includes a Sequence Listing.

(51) Int. Cl.
  *A61K 47/69* (2017.01)
  *A61P 15/06* (2006.01)
  *A61K 38/095* (2019.01)
  *A61K 9/127* (2006.01)
  *A61K 31/137* (2006.01)
  *A61K 31/4025* (2006.01)
  *A61K 31/405* (2006.01)
  *A61K 31/43* (2006.01)
  *A61K 31/4422* (2006.01)
  *A61K 31/545* (2006.01)
  *A61K 31/57* (2006.01)
  *A61K 31/7048* (2006.01)
  *A61K 33/06* (2006.01)
  *A61K 38/16* (2006.01)
  *A61K 38/45* (2006.01)
  *A61K 38/51* (2006.01)

(52) U.S. Cl.
  CPC .......... *A61K 31/57* (2013.01); *A61K 31/7048* (2013.01); *A61K 33/06* (2013.01); *A61K 38/095* (2019.01); *A61K 38/164* (2013.01); *A61K 38/168* (2013.01); *A61K 38/1709* (2013.01); *A61K 38/1774* (2013.01); *A61K 38/45* (2013.01); *A61K 38/51* (2013.01); *A61K 47/6911* (2017.08); *A61P 15/06* (2018.01)

(56) References Cited

OTHER PUBLICATIONS

Pirianov et al., "The Cyclopentenone 15-Deoxy-12,14-Prostaglandin J2 Delays Lipoplysaccharide-Induced Preterm Delivery and Reduced Mortality in the Newborn Mouse," Endocrinology, 150 (2): 699-706 (2009).

Zhong et al., "Toll-like receptor/NFKB inflammatory/miR-146a pathway contributes to the ART-correlated preterm birth butcome," Oncotarget, 7 (45): 72475-72485 (2016).

Office Action issued in corresponding Chinese Patent Application No. 2020800909840 dated Mar. 15, 2023.

\* cited by examiner

FIG. 1A
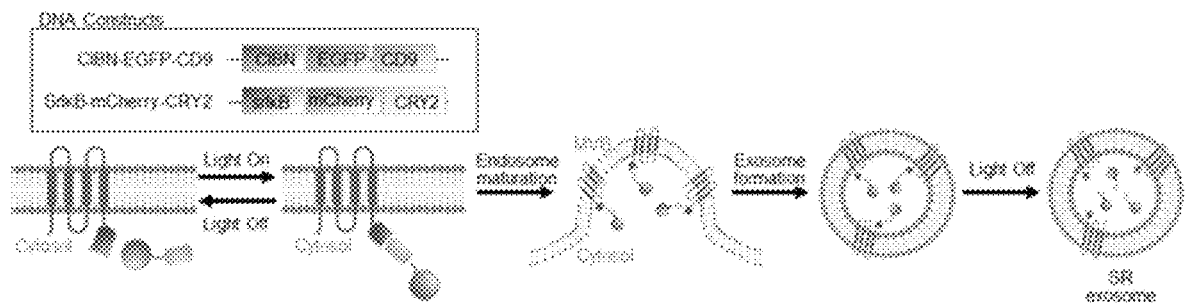
FIG. 1B
FIG. 1C
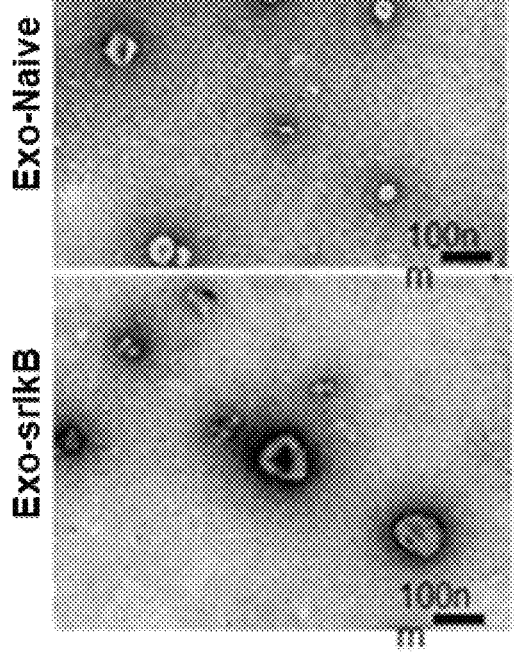
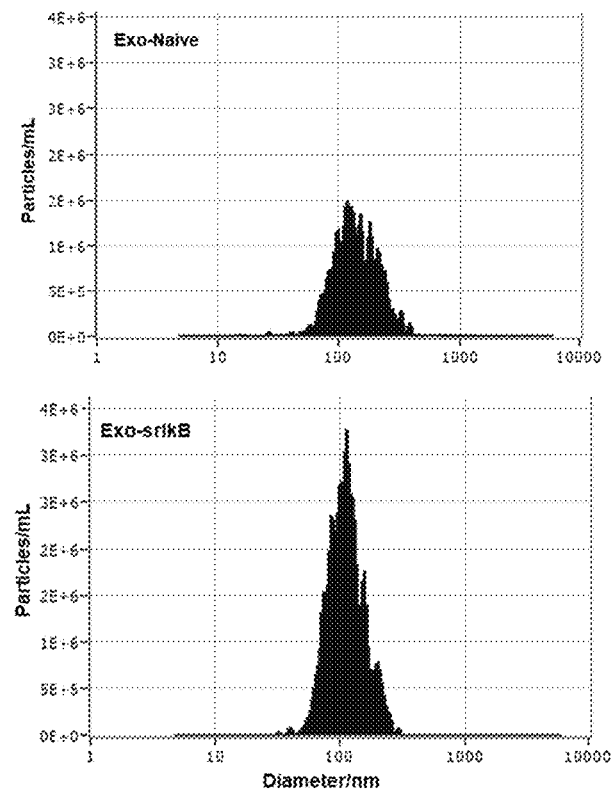

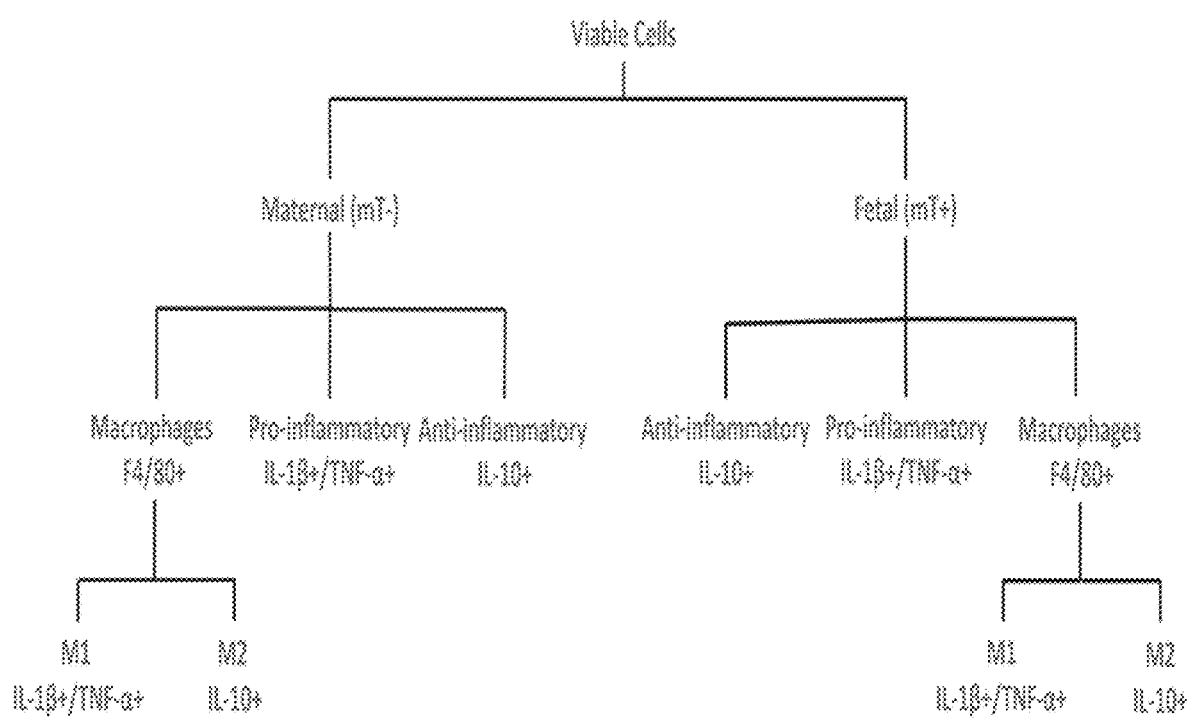

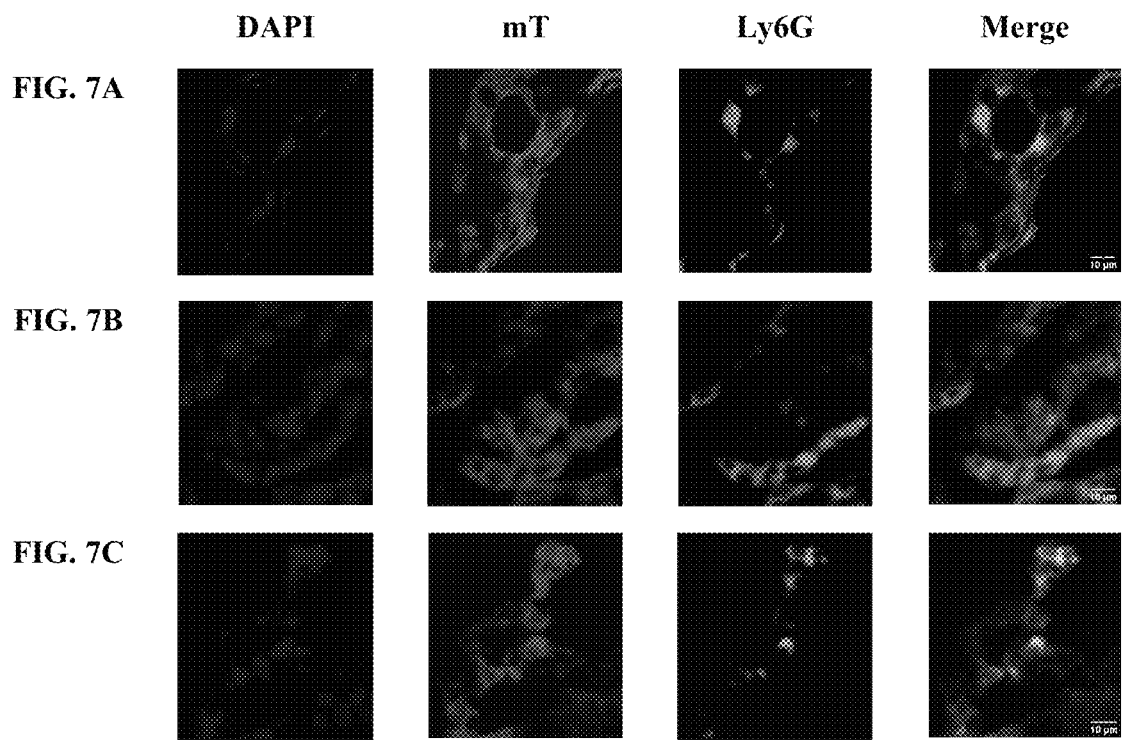
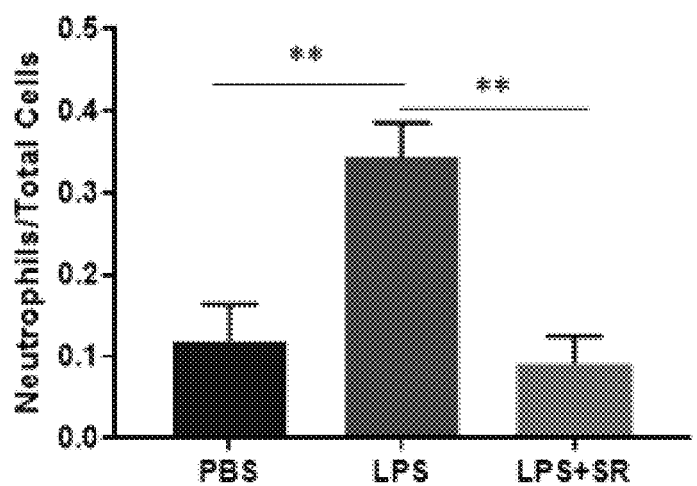

DAPI　　　mT　　　F4/80　　　Merge　　　3D Model

DAPI　　　mT　　　F4/80　　　Merge　　　3D Model

DAPI　　　mT　　　F4/80　　　Merge　　　3D Model

COMPOSITIONS CONTAINING EXOSOME CARRYING NF-κB INHIBITORS AND METHODS OF USING THEREOF

CROSS REFERENCE TO RELATED APPLICATIONS

This application claims priority to US Provisional Application Nos. 62/955,339, filed Dec. 30, 2019 and 63/105,207, filed Oct. 23, 2020, the contents of each of which are hereby incorporated by reference in their entireties.

FIELD OF THE INVENTION

The present invention is related to compositions containing extracellular vesicles (exosomes) carrying NF-κB inhibitors and methods of using the same for increasing lifespan of fetus, viability of fetus, or viability of newborn, for treating inflammation in uterus and/or fetus, for delaying preterm birth, or for treating a condition related to inflammation in uterus and/or fetus.

REFERENCE OF SEQUENCE LISTING

The present application contains a Sequence Listing which has been submitted in computer readable format, which is incorporated herein by reference in its entirety.

BACKGROUND OF THE INVENTION

Pregnancy is delicately balanced by various endocrine, paracrine, and immune systems. Disruption of balanced activities in various fetal and maternal intrauterine tissues primes them for parturition-associated changes. Intrauterine inflammation resulting from interrupted uterine homeostasis is one of the biologic effectors of parturition.

Parturition in all species is associated with inflammation characterized by infiltration and activation of immune cells in both fetal and maternal uterine tissues (uterus, cervix, decidua, and fetal membranes), along with an increase in proinflammatory cytokines and chemokines mediated by the pro-inflammatory transcription factor nuclear factor-κB (NF-κB), and a decrease in anti-inflammatory cytokines and chemokines. Inflammation that mechanistically contributes to parturition is expedited by both endocrine and paracrine mediators when fetal growth and maturation is complete. Premature disruption of immune homeostasis and overwhelming inflammation, either due to infection or other non-infectious risk factors prior to 37 weeks, often result in spontaneous early termination of pregnancy or preterm birth (PTB).

Preterm prelabor rupture of the fetal membranes (pPROMs) account for ~60% of all PTBs. The majority of spontaneous PTBs and pPROMs are associated with intra-amniotic infection that can override immune tolerance, causing a host inflammatory response.

Although leukocytes in fetal and maternal tissues have been studied for awhile, their origin (fetal vs maternal) is still unclear. The gaps in knowledge are primarily due to a lack of specific protein markers to consistently differentiate between fetal and maternal cells in vivo. A better understanding of the mechanistic contributions of fetal immune cells to parturition pathways in fetal and maternal tissues is essential to developing rational therapy to minimize inflammation and reduce the incidence of PTB.

The fetal inflammatory response due to infection and histologic chorioamnionitis (infiltration of polymorphonuclear leukocytes to the fetal membranes) is a major determinant of neonatal mortality and morbidity, that is often associated with PTB. Several studies are testing therapeutics that block inflammation by inhibiting the inflammatory transcription factor NF-κB using cytokine-suppressive anti-inflammatory drugs (CSAID). Very few of studies have progressed to clinical trials, and none are clinically in use, partly due to problems associated with half-life, mode of delivery, placental permeability, effectiveness in reducing the fetal inflammatory response, and teratogenicity of these proposed agents.

Treating the inflammation or infection in fetal and maternal tissues may delay a potential preterm delivery but does not provide information about the health of the fetus or newborn which is the goal of this treatment.

A variety of medications, including anti-inflammatory drugs and antibiotics have been tested to avoid unnecessary preterm births, but the problem remains unsolved. For example, medications such as anti-inflammatory drugs do not easily pass through the placenta. In addition, medications currently used for preterm birth-associated diseases must be carefully administered to avoid potential side effects including pulmonary edema, impaired renal function cardiovascular problems and metabolic disorders. Moreover, antibiotics used for the treatment of preterm complications, such as preterm labor, preterm endometriosis and preterm amnionitis, must be carefully prescribed to avoid side effects for the mother, fetus, and newborn.

Thus, there remains an ongoing and longstanding need for increasing lifespan of fetus, viability of fetus, or viability of newborn, for treating inflammation in uterus and/or fetus, for delaying preterm birth, or for treating a condition related to inflammation in uterus and/or fetus.

SUMMARY OF THE INVENTION

A certain embodiment of the present invention provides methods for increasing lifespan of fetus, viability of fetus, or viability of newborn, for treating inflammation in maternal and/or fetus, for delaying preterm birth, or for treating a condition related to inflammation in maternal and/or fetus comprising:

administering a composition comprising extracellular vesicles comprising a nuclear factor kappa beta (NF-κB) inhibitor; and a photo-specific binding protein, to a subject in need thereof.

Another embodiment of the present invention provides pharmaceutical compositions for increasing lifespan of fetus, viability of fetus, or viability of newborn; treating inflammation in uterus and/or fetus, delaying preterm birth; or treating a condition related to inflammation in uterus and/or fetus during pregnancy comprising:

extracellular vesicles comprising a nuclear factor kappa beta (NF-κB) inhibitor; and a photo-specific binding protein.

Other embodiment of the present invention provides a use of extracellular vesicles comprising a nuclear factor kappa beta (NF-κB) inhibitor; and a photo-specific binding protein for preparation of a pharmaceutical composition for increasing lifespan of fetus, viability of fetus, or viability of newborn; treating inflammation in uterus and/or fetus, delaying preterm birth; or treating a condition related to inflammation in uterus and/or fetus during pregnancy.

Yet another embodiment of the present invention provides methods for increasing lifespan of fetus, viability of fetus, or viability of newborn, for treating inflammation in uterus and/or fetus, for delaying preterm birth, or for treating a condition related to inflammation in uterus and/or fetus comprising:

administering a composition comprising extracellular vesicles comprising a nuclear factor kappa beta (NF-κB) inhibitor; and a photo-specific binding protein; and administering an antibiotic or a uterine contraction inhibitor with, before or after the administration of the composition comprising extracellular vesicles, to a subject in need thereof.

In certain embodiments, the invention provides a method for delivering a drug or drugs to the fetus and a method for increasing lifespan of fetus, viability of fetus, or viability of newborn, for treating inflammation in uterus and/or fetus, for delaying preterm birth, or for treating a condition related to inflammation in uterus and/or fetus.

In another embodiment, the invention provides a composition containing extracellular vesicles, including exosomes, to deliver cargo or drugs to maternal and fetal subjects for promoting functional improvements, including increasing lifespan of fetus, viability of fetus, or viability of newborn; treating inflammation in uterus and/or fetus; delaying preterm birth; or treating a condition related to inflammation in uterus and/or fetus.

In certain other embodiments, the invention provides an exosome carrying:

1) a first fusion protein having an exosome specific marker conjugated to a first photo-specific binding protein; and 2) a second fusion protein having an NF-κB inhibitory protein, or a fragment thereof, as an active ingredient conjugated to a second photo-specific binding protein.

In another embodiment, the invention provides a combination agent for increasing lifespan of fetus, viability of fetus, or viability of newborn, for treating inflammation in uterus and/or fetus, for delaying preterm birth, or for treating a condition related to inflammation in uterus and/or fetus, comprising an exosome carrying:

(i) a first component comprising an NF-κB inhibitory protein, or a fragment thereof; and (ii) a second component comprising an antibiotic or uterine contraction inhibitor as an active ingredient.

In certain other embodiments, the invention provides a combination agent for increasing lifespan of fetus, viability of fetus, or viability of newborn, for treating inflammation in uterus and/or fetus, for delaying preterm birth, or for treating a condition related to inflammation in uterus and/or fetus, comprising an exosome carrying:

(i) 1) a first fusion protein comprising an exosome specific marker conjugated to a first photo-specific binding protein; and 2) the first component comprising the second fusion protein having the NF-κB inhibitory protein or fragment thereof conjugated to the second photo-specific binding protein; and (ii) the second component comprising a uterine contraction inhibitor or an antibiotic, as an active ingredient.

The invention provides a therapeutic agent to delay preterm birth and preterm rupture of amniotic membrane and to regulate the levels of proinflammatory and anti-inflammatory cytokines in the cells of maternal plasma, uterus and cervix, and placental barrier between mother and fetus, so that it can be effectively used as an active agent by using an exosome carrying the NF-κB inhibitory protein or a fragment thereof is a therapeutic composition of preterm and preterm birth-associated diseases.

In yet another embodiment, the invention provides exosomes of 50-200 nm diameter size or 50-150 nm diameter size containing biologically active cargo for the compositions and method thereof.

In another certain embodiment of the invention, the exosomes are engineered to contain a mutant form of the biological inhibitor of NF-κB, called super repressor IκB (SR or srIκB, SEQ ID NO:1) (N. Yim et al., Nature Communications 7, 12277 (2016); H. Choi et al., Sci Adv 6, eaaz6980 (2020), contents of each of which are incorporated herein by reference In another embodiment, the invention provides fetal-specific trafficking of the engineered exosomes, methods for increasing lifespan of fetus, viability of fetus, or viability of newborn, for treating inflammation in uterus and/or fetus, for delaying preterm birth, or for treating a condition related to inflammation in uterus and/or fetus.

In one embodiment, the invention provides the composition comprising an exosome carrying NF-κB inhibitory protein or a fragment thereof as an active ingredient for for increasing lifespan of fetus, viability of fetus, or viability of newborn, for treating inflammation in uterus and/or fetus, for delaying preterm birth, or for treating a condition related to inflammation in uterus and/or fetus.

In certain embodiment, the invention provides a therapeutic agent to delay preterm birth and preterm rupture of amniotic membrane and to regulate the levels of proinflammatory and anti-inflammatory cytokines in the cells of maternal plasma, uterus and cervix, and placental barrier between mother and fetus, so that it can be effectively used as an active agent by using an exosome carrying the NF-κB inhibitory protein or a fragment thereof is a therapeutic composition of preterm and preterm birth-associated diseases.

BRIEF DESCRIPTION OF THE DRAWINGS

FIGS. 1A-1D show the characterization of engineered exosomes carrying the NF-κB inhibitor, super repressor IκB (SR or srIκB), using Exosomes for Protein Loading Via Optically Reversible Protein-Protein Interactions (EXPLOR) Technology.

FIG. 1A provides a schematic diagram of DNA constructs used to produce the super repressor IκB loaded exosome (Exo-srIκB) (upper) and a schematic diagram showing fusion proteins and their proposed activities of light-dependent protein-protein interactions to create Exo-srIκB (lower).

FIG. 1B provides a morphological characterization of naïve exosome (Exo-Naïve) and Exo-srIκB using transmission electron microscopy (TEM).

FIG. 1C provides a representative graph showing the size and concentration of naïve exosome (Exo-Naïve) and Exo-srIκB determined by nanoparticle tracking analysis (NTA).

FIG. 1D provides a result for protein profile of the exosome-producing cell and isolated exosomes by western blot, wherein HEK293T cells that stably express the fusion protein, mcherry-srIκB-CRY2 and CIBN-EGFP-CD9, and exosomes derived from theses HEK293T cells, were lysed and subjected to western blot against the indicated proteins. The common exosome markers, the tetraspanin TSG101 and CD63, and GAPDH were detected in cells and exosomes, whereas a Golgi-derived GM130 was only detected in the cell lysate.

FIG. 2A shows the survival rate of the fetus in the mice injected with phosphate buffered saline (PBS), lipopolysaccharide (LPS), or LPS+Exo-srIκB treatment groups at various routes of injection, wherein the groups are as follows:
(1) PBS: no LPS injection but only PBS injection;
(2) LPS: LPS injection but no further treatment;
(3) LPS+N IP: LPS injection followed by intraperitoneal injection of Exo-Naive;
(4) LPS+SR IP: LPS injection followed by intraperitoneal injection of Exo-srIκB;
(5) LPS+SR IV: LPS injection followed by intravenous injection of Exo-srIκB;
(6) LPS+SR IM: LPS injection followed by intramuscular injection of Exo-srIκB; and
(7) LPS+SR SubQ: LPS injection followed by subcutaneous injection of Exo-srIκB.

FIG. 2B shows hours of survival after LPS injection in the same groups in FIG. 2A.

FIG. 2C provides average maternal weight (left) and newborn pup weight (right). Data was analyzed using a one-way ANOVA with a Tukey's posthoc test.

FIG. 2D provides images of pups from PBS, LPS, and LPS+Exo-srIκB treatment groups at the time of collection on E16 (mouse embryonic day 16). For all groups are n≥4.

FIG. 5 shows a schematic diagram that was used to characterize inflammatory cells in maternal uterus and fetal membrane isolated from the mice of pregnancy model. Maternal and fetal inflammatory cells were analyzed for cell migration and profile change by flow cytometry.

FIG. 6A shows the ratio of fetal M1:M2 in uterus.
FIG. 6B shows the ratio of pro-inflammatory cells:anti-inflammatory cells in uterus.

FIG. 6C shows the ratio of M1:M2 in fetal membranes.
FIG. 6D shows the ratio of pro-inflammatory cells:anti-inflammatory cells in fetal membranes.

FIGS. 7A-7D show effect of Exo-srIκB treatment on neutrophil infiltration into fetal membrane and histologic chorioamnionitis (HCA). Fluorescence microscopy was used to colocalize the red fluorescent protein tdTomato (mT)-expressing cells with the neutrophil marker Ly6G (green membrane fluorescence) in PBS-injected mice (FIG. 7A), in LPS-injected mice (FIG. 7B), and in LPS+Exo-srIκB-injected mice (FIG. 7C). Scale bars represent 10 μm.

FIG. 7D shows the result of quantitation of colocalization for Ly6G+neutrophils in the fetal membranes in PBS-, LPS-, and LPS+Exo-srIκB (LPS-SR)-injected mice. For all experimental groups are n≥5 and data was analyzed using a one-way ANOVA with a Tukey's posthoc test.

FIG. 8A: Neutrophils in the placenta;
FIG. 8B: Neutrophils in the fetal membranes;
FIG. 8C: NK1.1+ and NK1.1+/DX5+ cells in the cervix;
FIG. 8D: NK1.1+ and NK1.1+/DX5+ cells in the placenta;
and
FIG. 8E: NK1.1+ and NK1.1+/DX5+ cells in the fetal membranes.

For all groups n≥4. Data are shown as mean±SEM. P values were calculated using a two-way ANOVA with a Tukey correction for multiple analysis. *P≤0.05P≤0.01*P≤0.001 ****P≤0.0001.

Figure 9A:
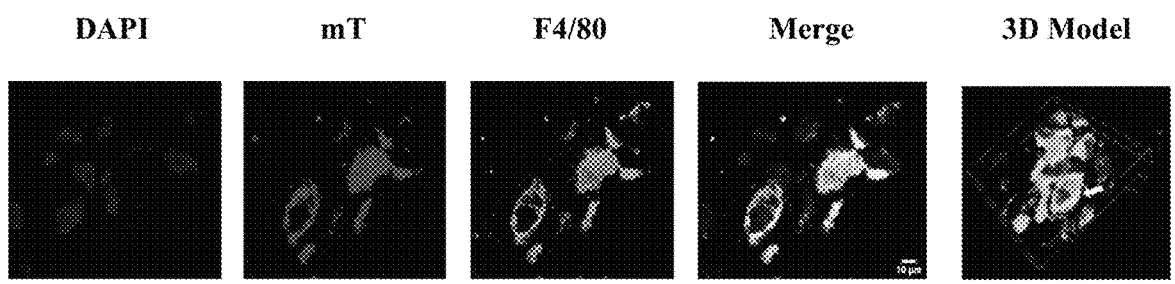
Figure 9B:
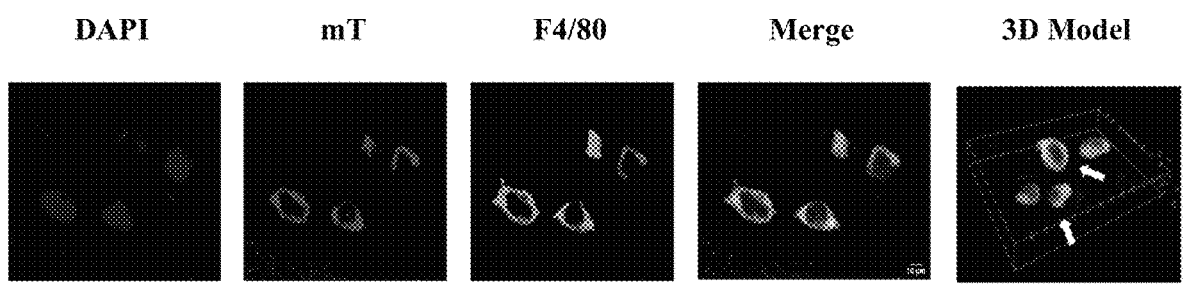
Figure 9C:
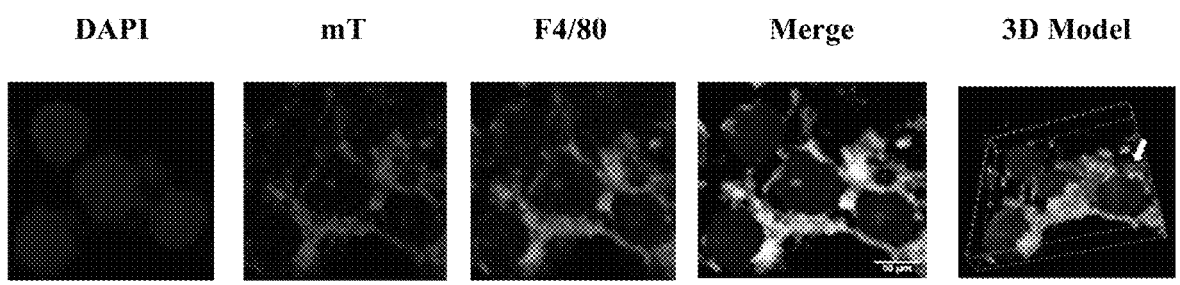

FIGS. 9A-9C shows fetal macrophages localized in maternal tissues.
FIG. 9A: Cervix;
FIG. 9B: uterus; and
FIG. 9C: decidua.

Arrows in 3 dimensional model of colocalization indicate fetal macrophages (mT+F4/80+).

Figure 10:
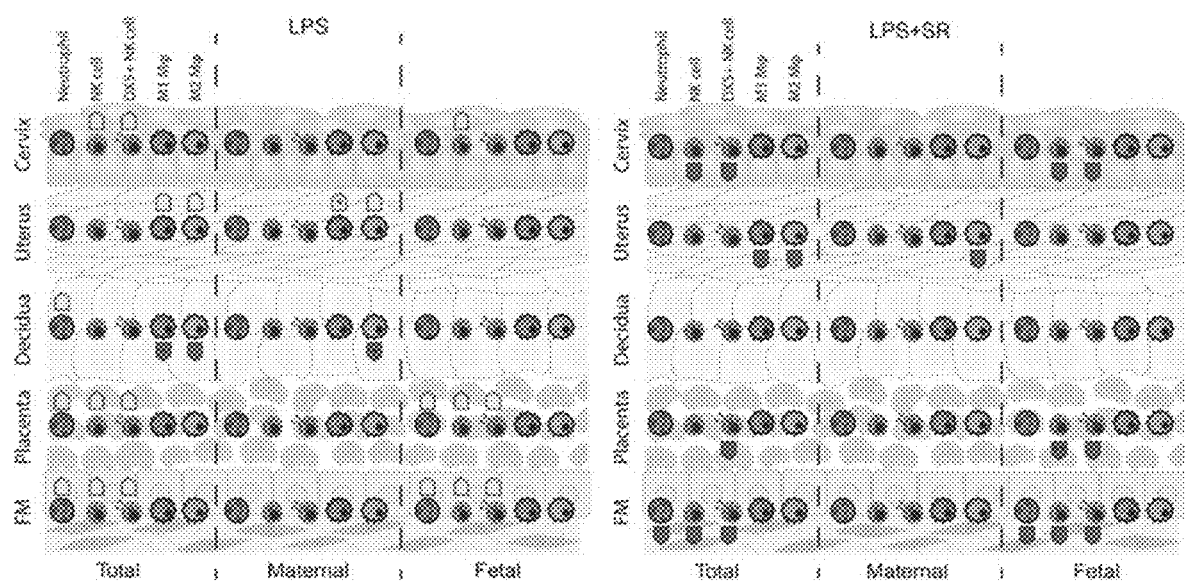

FIG. 10 shows effects of Exo-srIκB on immune cell infiltration in maternal and fetal tissues from LPS- and LPS+Exo-srIκB-injected groups. Immune cell infiltration is compared between LPS (left) and LPS+Exo-srIκB (shown as LPS+SR on the right) treatment, which is predominantly a fetal response and is reduced at the fetal-maternal interface with Exo-srIκB treatment. Immune cell infiltration of LPS-injected mice. Arrows indicate increase or decrease in number of cells. *P=0.07; **P=0.06.

Figure 11A:
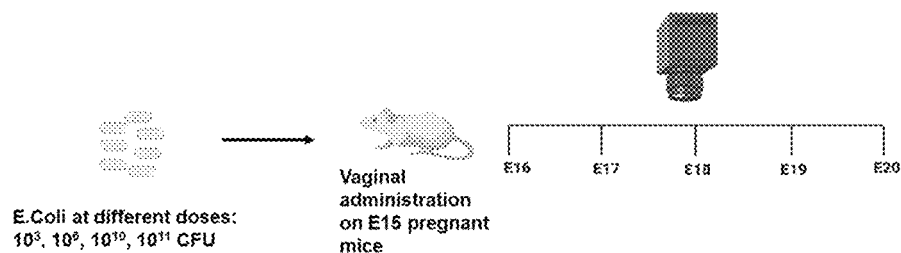

FIG. 11A presents the studies for determination of *E. coli* concentration: On day E15 (mouse embryonic day 15), pregnant CD 1 mice were injected with *E. coli* at a dose of 1E+03, 1E+06, 1E+10 and 1E+11 CFU/ml through vaginal administration. After administration mice were kept under video surveillance for monitoring preterm birth delivery.

Figure 11B:
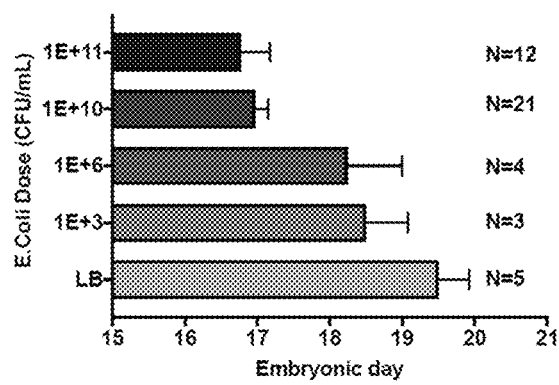

FIG. 11B presents the result of the most optimal concentration obtained, at 1E+11 CFU/ml of *E. coli*, to induce preterm birth.

DETAILED DESCRIPTION OF THE INVENTION

The present invention provides methods for increasing lifespan of fetus, viability of fetus, or viability of newborn, for treating inflammation in maternal and/or fetus, for delaying preterm birth, or for treating a condition related to inflammation in maternal, preferably uterus, but not limited to, and/or fetus comprising:

administering a composition comprising extracellular vesicles comprising a nuclear factor kappa beta (NF-κB) inhibitor; and a photo-specific binding protein,
to a subject in need thereof.

The present invention also provides pharmaceutical compositions for increasing lifespan of fetus, viability of fetus, or viability of newborn; treating inflammation in uterus and/or fetus, delaying preterm birth; or treating a condition related to inflammation in uterus and/or fetus during pregnancy comprising:

extracellular vesicles comprising a nuclear factor kappa beta (NF-κB) inhibitor; and a photo-specific binding protein.

Furthermore, present invention provides a use of extracellular vesicles comprising a nuclear factor kappa beta (NF-κB) inhibitor; and a photo-specific binding protein for preparation of a pharmaceutical composition for increasing lifespan of fetus, viability of fetus, or viability of newborn; treating inflammation in uterus and/or fetus, delaying preterm birth; or treating a condition related to inflammation in uterus and/or fetus during pregnancy.

In addition, the present invention provides methods for increasing lifespan of fetus, viability of fetus, or viability of newborn, for treating inflammation in uterus and/or fetus, for delaying preterm birth, or for treating a condition related to inflammation in uterus and/or fetus comprising:

administering a composition comprising extracellular vesicles comprising a nuclear factor kappa beta (NF-κB) inhibitor; and a photo-specific binding protein; and administering an antibiotic or a uterine contraction inhibitor with, before or after the administration of the composition comprising extracellular vesicles,
to a subject in need thereof.

In certain embodiments, the invention provides a method for delivering a drug or drugs to the fetus and a method for increasing lifespan of fetus, viability of fetus, or viability of newborn, for treating inflammation in uterus and/or fetus, for delaying preterm birth, or for treating a condition related to inflammation in uterus and/or fetus.

In another embodiment, the invention provides a combination agent for increasing lifespan of fetus, viability of fetus, or viability of newborn, for treating inflammation in uterus and/or fetus, for delaying preterm birth, or for treating a condition related to inflammation in uterus and/or fetus, comprising an exosome carrying:

(i) a first component comprising an NF-κB inhibitory protein, or a fragment thereof; and (ii) a second component comprising an antibiotic or uterine contraction inhibitor as an active ingredient.

In certain other embodiments, the invention provides a combination agent for increasing lifespan of fetus, viability of fetus, or viability of newborn, for treating inflammation in uterus and/or fetus, for delaying preterm birth, or for treating a condition related to inflammation in uterus and/or fetus, comprising an exosome carrying:

(i) 1) a first fusion protein comprising an exosome specific marker conjugated to a first photo-specific binding protein; and 2) the first component comprising the second fusion protein having the NF-κB inhibitory protein or fragment thereof conjugated to the second photo-specific binding protein; and (ii) the second component comprising a uterine contraction inhibitor or an antibiotic, as an active ingredient.

The invention provides a therapeutic agent to delay preterm birth and preterm rupture of amniotic membrane and to regulate the levels of proinflammatory and anti-inflammatory cytokines in the cells of maternal plasma, uterus and cervix, and placental barrier between mother and fetus, so that it can be effectively used as an active agent by using an exosome carrying the NF-κB inhibitory protein or a fragment thereof is a therapeutic composition of preterm and preterm birth-associated diseases.

In yet another embodiment, the invention provides exosomes of 50-200 nm diameter size or 50-150 nm diameter size containing biologically active cargo for the compositions and method thereof.

In another certain embodiment of the invention, the exosomes are engineered to contain a mutant form of the biological inhibitor of NF-κB, called super repressor IκB (SR or srIκB, SEQ ID NO:1) (N. Yim et al., *Nature Communications* 7, 12277 (2016); H. Choi et al., *Sci Adv* 6, eaaz6980 (2020).

In another embodiment, the invention provides fetal-specific trafficking of the engineered exosomes, methods for increasing lifespan of fetus, viability of fetus, or viability of newborn, for treating inflammation in uterus and/or fetus, for delaying preterm birth, or for treating a condition related to inflammation in uterus and/or fetus.

In one embodiment, the invention provides the composition comprising an exosome carrying NF-κB inhibitory protein or a fragment thereof as an active ingredient for for increasing lifespan of fetus, viability of fetus, or viability of newborn, for treating inflammation in uterus and/or fetus, for delaying preterm birth, or for treating a condition related to inflammation in uterus and/or fetus.

In certain embodiment, the invention provides a therapeutic agent to delay preterm birth and preterm rupture of amniotic membrane and to regulate the levels of proinflammatory and anti-inflammatory cytokines in the cells of maternal plasma, uterus and cervix, and placental barrier between mother and fetus, so that it can be effectively used as an active agent by using an exosome carrying the NF-κB inhibitory protein or a fragment thereof is a therapeutic composition of preterm and preterm birth-associated diseases.

Extracellular Vesicles

The present invention provides compositions comprising extracellular vesicles, preferably exosomes, effective for increasing lifespan of fetus, viability of fetus, or viability of newborn, for treating inflammation in uterus and/or fetus, for delaying preterm birth, or for treating a condition related to inflammation in uterus and/or fetus. The examples are presented using exosomes, but it is not limited to exosomes but can be extracellular vesicles known to the ordinary skill in the art to perform the similar function.

In certain other embodiments, the invention provides an exosome carrying:

1) a first fusion protein having an exosome specific marker conjugated to a first photo-specific binding protein; and 2) a second fusion protein having an NF-κB inhibitory protein, or a fragment thereof, as an active ingredient conjugated to a second photo-specific binding protein.

In the exosome used in the present invention, the photo-specific binding protein is a first photo-specific binding protein or a second photo-specific binding protein;

the first photo-specific binding protein is conjugated to an exosome specific marker to form a first fusion protein (fusion protein I); and the second photo-specific binding protein is conjugated to the NF-κB inhibitory protein to form a second fusion protein (fusion protein II);

the fusion protein I and the fusion protein II are linked reversibly through the first photo-specific binding protein and the second photo-specific binding protein;

the first photo-specific binding protein is conjugated to the exosome specific marker to be located in the direction toward inside of the exosome;

the first photo-specific binding protein and the second photo-specific binding protein are selected from the group consisting of cryptochrome-interacting basic-helix-loop-helix protein (CIB), N terminal domain of CIB (CIBN), phytochrome B (PhyB), phytochrome interacting factor (PIF), Flavin binding, Kelch repeat F-box 1 (FKF1), GIGANTEA, CRY2 cryptochrome 2 (CRY2) and photolyase-homologous region (PHR), wherein, the first photo-specific binding protein is CIB or CIBN and the second photo-specific binding protein is CRY2 or PHR, or the first photo-specific binding protein is CRY2 or PHR and the second photo-specific binding protein is CIB or CIBN; or wherein, the first photo-specific binding protein is PhyB and the second photo-specific binding protein is PIF or the first photo-specific binding protein is PIF and the second photo-specific binding protein is PhyB; or wherein, the first photo-specific binding protein is GIGANTEA and the second photo-specific binding protein is FKF1 or the first photo-specific binding protein is FKF1 and the second photo-specific binding protein is GIGANTEA;

the exosome specific marker is selected from the group consisting of CD9, CD63, CD81 and CD82; and the NF-κB inhibitor is selected from the group consisting of a NF-κB inhibiting drug, a NF-κB inhibitory protein or fragment thereof, and a mixture thereof.

The exosomes are engineered to comprise one or more NF-κB inhibitors, and when administered to a pregnant subject, enhance the health and viability of an at risk developing fetus and newborn infants and provides a method for increasing lifespan of fetus, viability of fetus, or viability of newborn, for treating inflammation in uterus and/or fetus, for delaying preterm birth, or for treating a condition related to inflammation in uterus and/or fetus.

As used herein, the term "exosome" refers to small, extracellular vesicles (EV) with a size ranging from about 50-200 nm.

Exosomes are released from all types of cells and can contain a variety of cellular constituents, including proteins, DNA and RNA. Exosomes offer distinctive advantages of providing a stable form for delivery of biomolecules, such as protein therapeutics, for in vivo administration.

Without listing all details, the contents of parent U.S. Pat. No. 10,702,581 are incorporated herein by reference to provide the compositions and methods for preparing the exosomes containing NF-kB inhibitors of the invention in HEK293 cells. In brief, a pair of proteins: an exosome specific marker and a cargo protein, such as an NF-κB inhibitor, are expressed in host cells selected to produce exosomes at a high concentration. The exosome specific marker is engineered to be expressed as a fusion protein including a photo-specific binding protein such as CIBN or CRY2 (these only bind in the presence of light of a specific wavelength). Once the host cells have produced exosomes and the pair of proteins, the host cells are irradiated by selective light wavelengths to induce the linkage of the exosome specific marker and the cargo protein to form a light-induced dimer protein. Then, the dimer enters the exosome by the action of the exosome specific marker. When the light irradiation is terminated, the dimer separates into the cargo protein and the photo-specific binding protein inside the exosome. As a result, exosomes containing a free cargo protein separated from the fusion protein can be prepared efficiently In a further embodiment of the invention, the inventive exosome further comprises a photo-specific binding protein, wherein, the photo-specific binding protein comprises a first photo-specific binding protein and a second photo-specific binding protein, which interact reversibly with each other upon irradiation;

the first photo-specific binding protein is conjugated to an exosome specific marker to form a first fusion protein (fusion protein I); and the second photo-specific binding protein is conjugated to the NF-κB inhibitory protein to form a second fusion protein (fusion protein II);

the fusion protein I and the fusion protein II are linked reversibly through the first photo-specific binding protein and the second photo-specific binding protein; or the first photo-specific binding protein is conjugated to the exosome specific marker to be located in the direction toward inside of the exosome.

The term "photo-specific binding protein" refers to the photo-induced heterodimeric proteins photo-induced homodimeric proteins. Two proteins of the different types can form heterodimeric proteins, or two proteins of the same types can form homodimeric proteins, when irradiated with light of a specific wavelength.

In a particular embodiment, the first photo-specific binding protein and the second photo-specific binding protein are selected from the group consisting of CIB (cryptochrome-interacting basic-helix-loop-helix protein), CIBN (N terminal domain of CIB), PhyB (phytochrome B), PIF (phytochrome interacting factor), FKF1 (Flavin binding, Kelch repeat, F-box 1), GIGANTEA, CRY2 (cryptochrome 2) and PHR (photolyase homologous region), but not limited thereto.

In another particular embodiment, the first photo-specific binding protein is CIB or CIBN and the second photo-specific binding protein is CRY or PHR; or the first photo-specific binding protein is CRY or PHR and the second photo-specific binding protein is CIB or CIBN.

In a further embodiment, the first photo-specific binding protein is PhyB and the second photo-specific bind protein is PIF or the first photo-specific binding protein is PIF and the second photo-specific binding protein is PhyB.

In a further embodiment, the first photo-specific binding protein is GIGANTEA and the second photo-specific binding protein is FKF1 or the first photo-specific binding protein is FKF1 and the second photo-specific binding protein is GIGANTEA.

As used herein, the term "light" refers to the light irradiated to temporarily combine the first photo-specific binding protein and the second photo-specific binding protein expressed in the exosome-producing cells. For example, blue, red, yellow light, preferably, blue light at 450-485 nanometers, more preferably, 488 nanometer wavelength. Certain wavelength light emissions can harm the cells.

In the invention, the term "exosome specific marker" means a protein that is abundantly present in the membrane of the exosome. The exosome specific marker is optionally selected from the group consisting of CD9, CD63, CD81 and CD82, but not limited thereto.

In certain embodiments, the invention provides exosomes of 50-200 nm diameter size or 50-150 nm diameter size containing biologically active cargo for the compositions and method thereof.

NF-κB Inhibitor

The present invention provides and uses extracellular vesicle containing a NF-κB inhibitor,
wherein,
the NF-κB inhibitor is selected from the group consisting of a NF-κB inhibiting drug, a NF-κB inhibitory protein or fragment thereof, and a mixture thereof;
wherein, the NF-κB inhibitory protein is selected from the group consisting of a super-repressor-IκB (SRIκB), IκB-α, IκB-ε and B cell lymphoma 3 (BCL3), a mutant thereof and a mixture thereof.

Broadly, a NF-κB inhibitor is selected from the group consisting of an NF-κB inhibitory drug, an NF-κB inhibitory protein or its fragment, and/or a mixture thereof.

In particular, the NF-κB inhibitory protein is selected from the group consisting of super-repressor-IκB, IκB-α, IκB-β, IκB-ε, BCL-3, a mutant thereof, and/or a mixture thereof.

In one embodiment, the NF-κB inhibitory protein is a super-repressor-IκB, but can also be any of the proteins that can binds to NF-κB and inhibit the activation of the NF-κB in the cytoplasm.

In another embodiment the exosomes of the invention contain a mutant form of the biological inhibitor of NF-κB, called super repressor (SR) IκB (srIκB, SEQ ID NO:1). The mutant super-repressor-IκB avoids phosphoration by IκB kinase (IKK) and decomposition by the proteasome.

In a further embodiment of the invention, srIκB mutein replaces Ser32 and Ser36 of IκB (SEQ ID NO:2) with Ala.
SEQ ID NO:1 Homo sapiens, super-repressor-IκB (srIκB)
MFQAAERPQEWAMEGPRDGLKKERLLDDRHDAGL-
DAMKDEEYEQMVKELQEIRLEPQEVPRGSEPWK-
QQLTEDGDSFLHLAIIHEEKALTMEVIRQVKGDL-
AFLNFQNNLQQTPLHLAVITNQPEIAEALLGAGC-
DPELRDFRGNTPLHLACEQGCLASVGVLTQS-
CTTPHLHSILKATNYNGHTCLHLASIHGYLGIV-
ELLVSLGADVNAQEPCNGRTALHLAVDLQNPD-
LVSLLLKCGADVNRVTYQGYSPYQLTWGRPSTR-
IQQQLGQLTLENLQMLPESEDEESYDTES EFTEFT-
EDELPYDDCVFGGQRLTL
SEQ ID NO:2 Homo sapiens, IκB-α
MFQAAERPQEWAMEGPRDGLKKERLLDDRHDSG-
LDSMKDEEYEQMVKELQEIRLEPQ EVPRGSEPW-
KQQLTEDGDSFLHLAIIHEEKALTMEVIRQVKGD-
LAFLNFQNNLQQTPLH LAVITNQPEIAEALLGAGC-
DPELRDFRGNTPLHLACEQGCLASVGVLTQSCT-
TPHLHSILKATNYNGHTCLHLASIHGYLGIVELL-
VSLGADVNAQEPCNGRTALHLAVDLQNPDLVS
LLLKCGADVNRVTYQGYSPYQLTWGRPSTRIQQ-
QLGQLTLENLQMLPESEDEESYDTES EFTEFTEDE-
LPYDDCVFGGQRLTL In a further embodiment, IκB-β comprises any polypeptides having the amino acid sequences of SEQ ID NOs:3-6. IκB-ε comprises a polypeptide having the amino acid sequence of SEQ ID NO:7.

In a further embodiment, the BCL-3 comprises a polypeptide having the amino acid sequence of SEQ ID NO: 8.

Method of Preparation of Extracellular Vesicles Containing an NF-kB Inhibitor

The invention comprises the exosome carrying NF-κB inhibitory protein or a fragment thereof can be prepared by a method comprising the following steps, but not limited thereto:

a) introducing a polynucleotide encoding a first fusion protein having an exosome specific marker and a first photo-specific binding protein and of it a polynucleotide encoding a second fusion protein having a NF-κB inhibitory protein or a fragment and the second photo-specific binding protein that can be conjugated to the first photo-specific binding protein into an exosome producing cell;

b) irradiating the exosome-producing cell with LED light to induce conjugation between the first photo-specific binding protein and the second photo-specific binding protein; and c) stopping irradiation after the production of the exosome in the exosome-producing cell is confirmed.

As used herein, the term "exosome producing cells" refers to cells capable of producing the exosome.

The exosome producing cells are T-lymphocytes, dendritic cells, macronuclear cells (megakaryocyte), macrophages, stem cells and tumor cells, but are not particularly limited B-lymphocytes. In one embodiment, the exosome producing cell is HEK293 cell including HEK293F or HEK293T cells, the immortalized cell line.

Use of the Extracellular Vesicles Containing an NF-kB Inhibitor

The present invention provides a method for delivering drug to the fetus and for improving lifespan of the fetus or viability of the fetus and the newborn.

In a still further embodiment, the invention provides a composition containing extracellular vesicles including exosomes to deliver NF-κB inhibitors, such as a drug, an inhibitory protein or a fragment thereof, to maternal and fetal units for causing functional changes.

A "subject" according to the invention is broadly contemplated to be any mammal that would benefit from administration of the inventive exosomes comprising NF-κB inhibitors. A subject according to the invention can be any mammal, male or female. For the purpose of treating or reducing the risk of a preterm delivery of a gestating fetus or infant, the subject is a female mammal carrying young. For human medicine, the subject is a pregnant woman at risk of a preterm delivery. For veterinary medicine, a subject also includes pregnant females that are non-human mammals at risk of preterm delivery, for which such treatment is desirable and effective. Thus, a subject can be any pregnant female domestic or wild mammal. Wild mammals include animals in captivity for which veterinary care is being provided, e.g., primates, such as monkeys, great apes, felines such as lions, tigers, other wild animals such as, elephants, zebras, camelids, canids such as wolves, aquatic mammals, such as dolphins, cetaceans, such as whales, and the like. Domestic animals may be pets, such as cats and dogs, economically useful domestic animals such as equines, bovines, swine, members of the genus Capra, such as goats, and any other mammal for which such treatment is desirable and effective.

In one embodiment, preterm birth refers to a birth that takes place before 20 to 37 weeks of pregnancy.

A subject according to the invention also includes mammals used in experimental model system (e.g., mice and rats in studies for screening, characterizing, and evaluating drugs) and other mammals used in testing, such as rabbits, guinea pigs, hamsters, cats, and apes such as chimpanzees, gorillas, and monkeys.

The invention provides that exosomes carrying an NF-κB inhibitory protein, such as the super-repressor-IκB (SR-exosome) can extend an at risk pregnancy in a subject by delaying preterm birth and preterm rupture of the subject's amniotic membrane.

In one embodiment, the administration of the SR exosome to mice in a preterm birth model (preterm birth induced by lipopolysaccharide "LPS" administration) result in extending the term of the pregnancy in the LPS mice, relative to untreated LPS mice. In addition, the SR exosome was found to decrease the NF-κB activity and to increase the levels of pro-inflammatory cytokines and anti-inflammatory cytokines.

The invention provides a composition for preventing or treating preterm birth and preterm birth-associated diseases, using an exosome carrying NF-κB inhibitory protein (IκB) or a fragment thereof as an active ingredient.

The exosome can be used for treating or diagnosing a particular disease because the exosome can act as a carrier of a protein or proteins of interest, and can deliver the protein(s) of interest to the target cells or tissues.

The invention provides a method for increasing lifespan of fetus, viability of fetus, or viability of newborn, for treating inflammation in uterus and/or fetus, for delaying preterm birth, or for treating a condition related to inflammation in uterus and/or fetus comprising:

administering compositions containing extracellular vesicles (exosomes) carrying NF-κB inhibitors to a subject in need thereof, wherein, the composition is administered via oral, transdermal, intraperitoneal, intravenous, intramuscular, subcutaneous, intrathecal, vaginal, intrauterine, or mixed routes.

In a further embodiment, the present provides a method for increasing lifespan of fetus, viability of fetus, or viability of newborn, for treating inflammation in uterus and/or fetus, for delaying preterm birth, or for treating a condition related to inflammation in uterus and/or fetus comprising:

administering compositions containing extracellular vesicles (exosomes) carrying NF-κB inhibitors, one or more antibiotics and/or a uterine contraction inhibitor to a subject in need thereof, simultaneously or separately, wherein the one or more antibiotics is/are selected from the group consisting of penicillins, cephalosporins, macrolides, lincosamides, carbapenems, glycopeptides antibiotics, aminoglycosides antibiotics, tetracyclines antibiotics, erythromycin, nitroimidazoles, β-lactamase inhibitors, a derivative thereof, and a mixture thereof; and the uterine contraction inhibitor is selected from the group consisting of progesterone, nifedipine, atosiban, ritodrine, indomethacin, magnesium sulfate, orciprenaline, terbutaline, salbutamol, fenoterol, nylidrin, isoxsuprine, hexoprenaline, and a mixture thereof, but not limited to.

In certain embodiments, the antibiotics are penicillins, cephalosporins, macrolide antibiotics, lincosamides, carbapenems, glycopeptides, aminoglycosides, tetracyclines, nitroimidazoles, or two or more combinations thereof, but not limited to. For example, penicillins include penicillin G, penicillin V, ampicillin, amoxicillin, or piperacillin; cephalosporins include cefazolin, cefuroxime, cefotetan, cefmetazole, cefotaxime, ceftizoxime, ceftriaxone, ceftazidime, cefoperazone, cefromerome, cefepime, cephalexin cephradine, cefadroxil, cefaclor, cefprozil, loracarbef, cefpodoxime, cefpodoxime, or cefixime; macrolides include erythromycin, clarithromycin, tylosin, josamycin or leucomycin; lincosamides include lincomycinor clindamycin; carbapenems include imipenem, meropenem, doripenem or ertapenem; glycopeptides may include teicoplanin; aminoglycosides include gentamycin, tobramycin or amicasin; and tetracyclines include tetracycline, demeclocycline, methacycline, doxycycline or minocycline, but not limited thereto.

In a particular embodiment, the antibiotic is a penicillin or a β-lactamase inhibitor.

In a certain embodiment, the invention utilizes 0.1-150 mg/kg, 1-100 mg/kg, 5-75 mg/kg, 5-50 mg/kg, 7-20 mg/kg, or 10-15 mg/kg dose of an antibiotic, a tocolytic agent or uterine contracting inhibitor.

In a certain embodiment of the present invention, the composition is a pharmaceutical composition and administered in a pharmaceutically effective amount. As used herein, "pharmaceutically effective amount" refers to sufficient amount to treat the disease at a reasonable benefit/risk rate applicable to medical treatment, the effective amount is determined depending on patient's type of disease, disease severity, activity of the drug, sensitivity to the drug, time of administration, route of administration and exudation rate, treatment duration, additional drugs used at the same time as well as the factors well-known in the medical fields. As used herein, the compositions of the invention may be administered as the individual therapeutic agents or in combination with other therapeutic agents. The pharmaceutical composition used in combination with conventional therapeutic agents may be administered sequentially or simultaneously, and in a single time or multiple times. it is important to administer the amount of the composition that is having the maximum effect in a minimum amount without side effects in consideration of all of the factors described above, which can be easily determined by those skilled in the art.

The pharmaceutical composition comprising the inventive NF-κB inhibitory exosome may include pharmaceutically acceptable carriers, excipients and additives as needed to formulate the exosomes for oral administration, for injection or for infusion. These include, for example, stabilizers, surfactants, stiffening agents, lubricants, solubilizers, buffer agents, suspending agents, antioxidants, wetting modifiers, antifoam agents, preservatives, buffers, isotonic buffer solution, pH modulators and the like. For oral formulations, coatings, flavorings and sweeteners are optionally included.

Pharmaceutical compositions of the invention are preferably administered to a human subject of less than 20 to 34 weeks of pregnancy.

The pharmaceutical compositions of the invention can be administered orally, by infusion, parenterally or by any other art-known route of administration. Additional routes of administration include, for example, transdermal, intraperitoneal, intravenous, intramuscular, subcutaneous, intradermal, vaginal, or intrauterine administration. In addition, the pharmaceutical composition may be administered by any device that can make the active ingredient move to the target cell.

The dosage form of the pharmaceutical composition herein may be appropriately selected, depending on the formulation methods, administration method, patient's age, weight, disease, symptoms, and severity of the symptoms, but are and is not particularly limited. For instance, oral administration by tablets (including sublingual and effervescent tablets), granules, acids, liquids, syrups (including dry syrups), jelly agents, capsules (including soft capsules, micro capsules); injection (subcutaneous injections, intravenous, intramuscular, intraperitoneal and etc.), and non-oral administration by vaginal tablets, vaginal ointments/creams, vaginal rings, vaginal gels or vaginal foaming agents, vaginal inserts suppositories (including rectal suppositories, vaginal suppositories), intrauterine delivery system, inhalers, transdermal absorbers, eye drops andnasal drops.

The dosages of the pharmaceutical composition herein are appropriately determined depending on the patient's age, gender, weight, disease, symptoms, and severity thereof. In general, 0.05-150 mg per kg body weight, 0.1 mg to 100 mg per kg body weight, or 0.5 mg to 50 mg kg body weight can be administered daily, every other day, once a day or in a number of times, but are limited to the scope of the invention.

The formulations of the pharmaceutical composition herein may include the additives known in the art. For example, solid formulations for the oral administration can be prepared in the form of tablets, pills, granules, powders and capsules by adding excipients, binders, disintegrants, active agents, colorants, flavors, and/or fragrances to the active ingredient, followed by molding, assembly, or encapsulation in accordance with the conventional methods. An oral liquid formulation of the oral administration can be prepared in the form of oral liquid syrup by adding solvents (e.g., purified water or ethanol), dissolving supplements, suspension agents, flavors, buffers, isotonic agents, stabilizers, and/or fragrances to the active component, followed by crude fluid distribution in accordance with the conventional methods. A solution of injection administration can be prepared by mixing pH adjusters, buffers, stabilizers, isotonic agents, and/or local anesthetics with the active agent prepared by aseptic incorporation in the container, subcutaneous, intramuscular, and intravenous lysis in accordance with the conventional methods. Rectal suppositories can be prepared by adding mixing excipients and surfactants to the active component, followed by mixing and molding in accordance with the conventional methods. An ointment formulation can be prepared in the form of paste, cream and gel by adding bases such as white Vaseline or paraffin, stabilizers, wetting agents, preservatives such as methylperoxybenzoic acid to the active ingredient in accordance with the conventional methods.

The invention further provides a combination agent for preventing or treating preterm birth and preterm birth-associated diseases, comprising a first component comprising an exosome carrying NF-κB inhibitory protein or a fragment thereof; and a second component comprising an antibiotic or a uterine contraction inhibitor as an active ingredient.

More specifically, the invention provides a combination of agents for preventing or treating preterm birth and preterm birth-associated diseases, comprising an exosome carrying (i) 1) the first fusion protein having an exosome specific marker and the first photo-specific binding protein; and 2) the first component comprising a second fusion protein having a NF-κB inhibitory protein or a fragment thereof and a second photo-specific binding protein; and (ii) a second component carrying an antibiotic or a uterine contraction inhibitor as an active ingredient.

The invention provides a method of producing the exosome carrying the NF-κB inhibitory protein or a fragment thereof, for treating preterm birth-associated diseases, and the dosage form of the first component and second component. The formulation method is as described hereinbelow.

In the invention, the compositions containing extracellular vesicles (exosomes) carrying NF-κB inhibitors and an antibiotic and/or a uterine contraction inhibitor to a subject in need thereof, are administered simultaneously, separately, or sequentially.

As used herein, the term "simultaneously" refers to the administration of the antibiotic and/or the uterine contraction inhibitor of the pharmaceutically effective amount immediately or after a certain interval after administration of the compositions containing exosomes carrying NF-κB inhibitors of the pharmaceutically effective amount. Alternatively, the compositions containing exosomes carrying an NF-κB inhibitor can be administered immediately after the second component is administered or after a certain interval after the antibiotics and/or the second component is administered.

As used herein, the term "separately (including continuous or subsequent administration)" refers to the administration of an antibiotics and/or a uterine contraction inhibitor of a pharmaceutically effective amount after a certain period of time after the administration of the compositions containing exosomes carrying NF-κB inhibitors of the pharmaceutically effective amount is discontinued. Alternatively, the compositions containing exosomes carrying NF-κB inhibitors can be administered after a certain period of time after the administration of the antibiotics and/or a uterine contraction inhibitor is then discontinued. In addition, the term "after a specific period of discontinuation" refers to the time between the administrations of the compositions containing exosomes carrying NF-κB inhibitors and the antibiotics and/or a uterine contraction inhibitor. The specific period herein may be hours, days, weeks, or months.

The exosome carrying the NF-κB inhibitory protein can delay the preterm birth and preterm rupture of amniotic membrane, and regulate the levels of pro-inflammatory cytokines and anti-inflammatory cytokines in the maternal plasma, uterus and cervix as well as the placental barrier between mother and fetus. The NF-κB inhibitory protein or the fragment thereof is contained inside the exosome. Furthermore, an antibiotic or uterine contraction inhibitors can be used as an active ingredient in combination with NF-κB inhibitory protein for preventing or treating preterm birth and preterm birth-associated diseases.

In a further embodiment, the invention provides fetal-specific trafficking of the engineered exosomes, methods for treating infection and inflammation in the maternal units and fetus, for improving viability of the fetus, for increasing survival time of the fetus, for improving viability of the newborn.

In certain embodiments, the preterm birth-associated diseases include prenatal inflammation (prenatal inflammatory response), preterm labor, preterm delivery, preterm birth, preterm rupture of amniotic membrane, low birthweight and fetal inflammatory response syndrome (FIRS) by uterine fibroids.

In a further embodiment, prenatal inflammation response includes intrauterine inflammation, chorioamnionitis, amnionitis, amniotic fluid infection, placental infection, and intra-amniotic infection.

Without wishing to be being bound by any theory or hypothesis as to the operation of the invention, the invention provides compositions comprising srIκB loaded exosomes (Exo-srIκB) to effectively improve viability of fetus and health of the newborn by delaying infection-induced PTB in mouse models, or by reducing the fetal and maternal inflammatory response (innate immune cell trafficking and inflammatory cytokine production), but not limited thereof. The invention effectively delivers srIκB for a reduction in fetal innate cell migration and the inflammatory response in various fetal and maternal tissues.

More specifically, the invention reduces fetal immune cell trafficking to reduce inflammation in fetus as well as in maternal units, and to increase life-span of the fetus to improve health of newborn by administering the composition of the invention comprising exosome containing NF-κB inhibitory drugs.

The invention also provides sustained release of the therapeutically effective drugs, while conventional sustained effects required repeated dosing of the therapeutics.

Furthermore, the invention provides a composition and method for improving viability of the fetus and the newborn by prolongation of gestation, decreased proinflammatory factors such as including, but not limited to, interleukin-1β (IL-1β), interleukin-6 (IL-6), and interleukin-8 (IL-8) and increased anti-inflammatory factors including, but not limited to, interleukin-10 (IL-10), by treating with Exo-srIκB. Fetal innate immune cells trafficking to maternal uterine tissues and LPS-induced PTB was dominated by fetal, not maternal, innate immune cells in fetal and maternal tissues. The capacity of the fetal immune cells to respond and migrate to various fetal and maternal tissues indicates a functionally active fetal immune system in utero. Tropism of fetal innate immune cells to specific maternal uterine tissues after LPS challenge was tissue dependent.

Studies have shown that the prognosis of these complications is affected by intrauterine environment. In fact, the intrauterine environment, including intrauterine infections and inflammation, uterine ischemia, uterine excess expansion, abnormal allogenic awareness and allogenic reactions, cervical diseases and endocrine disorders, is a variety of pathological causes that result in preterm birth and a number of prenatal complications and affects mortality. Prenatal inflammatory responses known as intrauterine inflammation, chorioamnionitis, amnionitis, amniotic fluid infection, placental infection and intra-amniotic infection are mainly caused by bacterial infection through the vagina and cervix and often preceded by preterm amniotic rupture. Bacteria that infect uterus are first confined on the decidua-chorionic villi membrane, invades the amniotic membrane and causes inflammation, and then penetrate umbilical cord and cause inflammation in the umbilical cord (funisitis). This inflammation also affects the fetus. Intrauterine infection or inflammation activates the fetal congenital (innate) immune system which leads to "fetal inflammatory response syndrome (FIRS)." The original definition of FIRS refers to the high concentration of interleukin-6 (IL-6) (≥11 pg/mL) in the umbilical cord, but recent studies have shown that FIRS has been associated with tumor necrosis factor α (TNF-α), interleukin-1β (IL-1β), interleukin-8 (IL-8) and c-reactive protein (CRP). The fetuses with FIRS have been known to have the high rate of neonatal respiratory distress syndrome (RDS), neonatal sepsis, pneumonia, bronchopulmonary dysplasia (BPD), intraventricular hemorrhage (IVH), proliferative verrucous leukoplakia (PVL), cerebral palsy, necrotizing enterocolitis and retinopathy of prematurity (ROP).

Reduction of viability of the fetus and decreased health of the newborn is caused by a multiple reason with multiple etiologies, including, but not limited to, infection and the subject host's inflammatory response to infections. Although immune cell activation and migration are reported in fetal and maternal uterine tissues, specific contributions of the fetal innate immune cells in determining pregnancy outcomes remain elusive. Early termination of pregnancy rates have not improved in the past few decades and suggest a unmet need and a better understanding of the pathways, specifically fetal immune signaling-associated with reduced survival rate of the fetus, which is, in part, due to the inability to distinguish between fetal and maternal immune cells.

The below experiments confirm that the invention increases fetal lifespan in a lipopolysaccharide (LPS) model for preterm delivery. This suggests that inhibition of the fetal innate immune response may impact the delivery of viable newborns. The invention also suggests, without wishing to be bound to any theory or hypothesis, that the fetal inflammatory response primes maternal uterine tissues to transition them to a parturition phenotype. Again, wishing to be bound to any theory or hypothesis, this inflammatory response is in response to the presence of risk factors for reduction of fetal lifespan (e.g., infection), fetal tissue senescence, or signals of organ maturation capable of creating nuclear factor kappa B protein (NF-κB) activation in the fetal membranes and placenta.

Relationship Between Maternal and Fetal Immune Systems

Fetal microchimerism is defined as the persistence of fetal cells in maternal organs and circulation without any graft-versus-host reaction or rejection. Fetal microchimerism and characteristics of fetal immune cells in the maternal compartment have been studied in normal and preterm pregnancies. However, their functional role is still unknown. The immune status is often determined after the incident (e.g. term or preterm birth in humans) and/or following animal sacrifice subsequent to specific experimental exposures. As real-time measurements of cell trafficking at the tissue level are not practical, the critical window during the change in immune status is often missed, especially in response to an infection. This is likely due to a lack of markers that are indicative of the fetal-specific immune response and the impracticality of longitudinal sampling of fetal biological samples during pregnancy. Thus, the fetal immune system has been an unrecognized critical aspect of maternal-fetal tolerance and the onset of uterine contractions.

Very few studies have attempted to evaluate the fetal vs maternal immune response under adverse pregnancy conditions. Studies by Gomez-Lopez et al.→citation? used DNA fingerprinting and the Y-chromosome FISH to show that neutrophils in the amniotic fluid are from both the fetus and the mother and they can contribute to the inflammatory response associated with intra-amniotic infection. Gomez-Lopez et al. highlighted the cause vs. effect issue as fetal tissue samples were obtained after term or PTB, and, as such, a critical window of immune status change is difficult to determine with post-delivery samples. Such post-delivery samples may have been confounded with a multitude of labor-related factors, especially in response to an intra-amniotic infection.

Based on the known analytical method and the result, the HCA data of the invention confirms that fetal neutrophils are primarily responsible for the immune cell infiltration of the fetal membranes. Although no major shift in macrophage populations in the mouse models of preterm birth (PTB) has been known, predominance of fetal macrophages compared to maternal macrophages was found in the amniotic fluid of women with documented intra-amniotic infection and inflammation. An animal model for induced preterm labor can be created by injection of E. coli into a mouse with a genetic knockout of MyD88. MyD88 is one of the key components needed for NF-κB activation. When combined with E. coli injection a mouse model for induced preterm labor is created. However, E. coli-induced PTB in the mouse is dependent on maternal and not fetal MyD88 expression, suggesting maternal, and not fetal, inflammatory contributions to PTB. Without bound to a theory, the fetus can signal readiness for delivery by an influx of immune cells to the maternal uterine compartments. However, maternal uterine tissues must generate an inflammatory response to transition a quiescent myometrium and cervix to a laboring phenotype in response to these fetal immune signals. It is likely that maternal MyD88 knockout blocked PTB in the Filipovich model due to the lack of localized maternal uterine inflammation by NF-κB responder genes, such as inflammatory cytokines, COX-2, and MMP9. These gene activations are essential for myometrial contractility and cervical remodeling. It was reported that placental inflammation is likely mediated through a TLR-MyD88-independent mechanism in response to LPS, which may negate the effect of a MyD88 knockout fetus. These data, therefore, create ambiguity with respect to MyD88-mediated fetal vs maternal effects.

These differences can be attributed to multiple factors, including mouse strain, stimulant used, and timing. In the invention, studies showed that inflammation on the maternal side is not a requirement for labor but a consequence of labor, and other studies showed decidual neutrophil infiltration is not required for PTB.

The invention provides, without any intention of being bound to a theory or hypothesis, that the fetal inflammatory response primes a maternal quiescent immune system to transition to an active state, and maternal-specific immune activation is not necessary.

Animal Models

The animal models used in the invention may not directly represent human term or preterm parturition. Injection of LPS or live bacteria, irrespective of route of administration, does not mimic infection/inflammation associated PTB in humans. However, it is understood by those skilled in the art that mouse models and other animal models have provided valuable information to help understand the mechanisms often seen in humans (specifically, paracrine and immune functions). Although NF-κB is widely studied as a mediator of pro-inflammatory responses, it is a ubiquitous molecule involved in multiple alternative pathways, including apoptosis and cell proliferation.

Even though the experimental data in the invention was restricted to innate immune cells, it will also be understood by those skilled in the art that the result can be interpreted and adapted to human cells with the knowledge well known in the art. The adaptive immune response, either independently or induced in response to innate cell infiltration or activation, is still a mechanism associated with labor at term and preterm.

EXAMPLES

The following examples are merely exemplary in nature and is not intended to limit application and uses. The following examples further illustrate the invention without, however, limiting the scope of the invention thereto. Various changes and modifications can be made by those skilled in the art on the basis of the description of the invention, and such changes and modifications are also included in the invention.

Example 1. Materials and Methods

Example 1-1. Characterization and Analysis of Exosomes Containing SR

Transmission Electron Microscopy (TEM) of Exosomes to Determine Size and Morphology Exosomes from stable cell lines were imaged using transmission electron microscopy (TEM) to determine the morphology, according to previous work, but with some modifications (H. Choi et al., Exosome-based delivery of super-repressor IκBα relieves sepsis-associated organ damage and mortality. Sci Adv 6, eaaz6980 (2020)). Briefly, 5 μL of exosomes suspended in phosphate buffer solution (PBS) were loaded onto glow-discharged carbon-coated copper grids (Electron Microscopy Sciences, Hatfield, USA). The grid was blotted with filter paper, then stained with 2% uranyl acetate. Samples were dried for 20 seconds, and then viewed with a Tecnai G2 Retrofit (FEI, Hillsboro, Oreg.).

Nanoparticle Tracking Analysis (NTA) to Determine Exosome Size and Concentration Nanoparticle tracking analysis (NTA) was performed using the ZetaView® PMX 110 (Particle Metrix, Meerbusch, Germany) and its corresponding software (ZetaView® 8.02.28). Frozen exosomes in 1×PBS were thawed on ice. All samples were diluted between 1:100 and 1:10,000 in 0.2 μm filtered PBS between 1:100 and 1:10, 000. For each measurement, two cycles were performed by scanning 11 cell positions with the following settings: focus: autofocus; camera sensitivity for all samples: 78.0; shutter: 70; cell temperature: 25° C. The instrument was cleaned between samples using filtered water. The results of the ZetaView® were used to calculate the number of exosomes used for in vivo studies.

Western Blot for the Analysis of SR in the Exosomes

To analyze the expression of exosome proteins, equal concentrations of the exosomes were mixed with sample buffer and boiled for 5 min. Antibodies targeting the following proteins were used: mCherry (ab125096; Abcam, Cambridge, United Kingdom), GFP (CST2555; Cell Signaling Technology, Danvers, Mass.), TSG101 (ab228013; Abcam), CD63 (sc-15363; Santa Cruz Biotechnology), GAPDH (sc-47724; Santa Cruz), and GM130 (ab52649; Abcam). Rabbit polyclonal anti-srIκB a antibody was generated using recombinant srIκB a peptide DRHDAGL-DAMKDE (SEQ ID NO:9) and affinity chromatography (AbClon, Seoul, South Korea).

Example 1-2. Animal Care

All animal procedures were approved by the Institutional Animal Care and Use Committee (IACUC) at the University of Texas Medical Branch, Galveston. Mice were housed in a temperature- and humidity-controlled facility with 12:12 h light and dark cycles. Regular chow and drinking solution were provided ad libitum. For preterm labor studies, timed pregnant CD-1 mice (stock 022, Charles River, Houston, Tex.) were used. For immune cell trafficking studies, transgenic C57BL/6J mice were used a with a plasma membrane-targeted, two-color, fluorescent Cre-reporter allele, where tandem dimer Tomato (mT) fluorescence is expressed in the cell membrane of all cells and tissues (stock 007676, Jackson Laboratory, Bar Harbor, Me.). The red fluorescent protein, mT, which is expressed in all cells and tissues, has increased brightness and photostability compared to other red fluorescent proteins. Breeding was performed in our facility, in which wild type (WT) C57BL/6J females (stock 000664, Jackson Laboratory), 8-12 weeks old, were mated with males that were homozygous for mT. Female mice were checked daily between 8:00 am and 9:00 am for the presence of a vaginal plug, indicating gestation day (E) 0.5. Females positive for a plug were housed separately from the males. Their weight was monitored, and a gain of at least 1.75 g by E10.5 confirmed pregnancy. Prior to tissue collection, animals were sacrificed by $CO_2$ inhalation according to the IACUC and the American Veterinary Medical Association guidelines.

Example 1-3. Lipopolysaccharide (LPS)-Treatment and SR Exosome Injections

On E15 (mouse embryonic day 15), equivalent to ~75% completed gestation in mice or ~28 weeks in humans, pregnant dams were intraperitoneally (i.p.) injected with one of the following: PBS or Lipopolysaccharide (LPS, serotype 055:B5, Sigma-Aldrich, St. Louis, Mo. [100 μg for CD-1 mice and 2.5 μg for WT mice]). Thirty minutes post-injection, animals were IP injected with either PBS, naïve exosomes, or SR exosomes (naïve and SR at $1 \times 10^{10}$ exosomes in 100 μL). PBS/naïve/SR exosome injections were repeated every 2 hours for a total of 5 injections.

Animals were monitored for preterm delivery, which was defined as delivery of at least one pup on or before E18.5, using Wansview® Wireless cameras (Shenzhen, China). A subset of CD-1 mice was euthanized at the time of LPS-induced preterm labor (12 hours post injection), and plasma was collected for cytokine analysis. A subset of WT mice was euthanized 24 hours post-LPS injection (E16 (mouse embryonic day 16), ca. 80% completed gestation in mice or ca. 30 weeks in humans) to determine fetal and maternal immune cell profile changes in fetal and maternal tissues.

Example 1-4. Luminex Assay to Determine Cytokine Concentration in Maternal Plasma Plasma collected from mice on E15 (mouse embryonic day 15, at time of LPS delivery) were assayed for IL-10, IL-6, IL-8, TNF-α, and IL-1β (n=3 per group) using MIL-LIPLEX® Mouse Cytokine Panel 1 (Millipore), following the manufacturer's protocol. Standard curves were developed using duplicate samples of known-quantity recombinant proteins that were provided by the manufacturer. Sample concentrations were determined by relating the absorbance of the samples to the standard curve using linear regression analysis.

Example 1-5. Immunofluorescent Staining and Colocalization of mT with Macrophages and Neutrophils in Maternal and Fetal Tissues For macrophage and neutrophil colocalization with mT, fresh tissue samples were washed with cold PBS then collected and embedded in optimal cutting temperature (OCT) compound and stored at −80° C. until use. OCT-embedded tissues were cut into 10-μm sections, then incubated at 55° C. for 15 min before fixing with 4% paraformaldehyde for 15 min at room temperature. Slides were washed twice in 1×Tris buffered saline with 0.1% Tween 20 (TBST), then sections were incubated with blocking buffer (3% bovine serum albumin (BSA) in TBST) for 1 hour at room temperature in a humidity chamber. The blocking buffer was removed, and macrophages were labeled with Alexa Fluor 488 conjugated anti-F4/80 (50-167-58, Thermo Fisher, Hampton, N.H.), while neutrophils were labeled with FITC-conjugated anti-Ly6G (551460, BD Biosciences, La Jolla, Calif.) and fetal cells were labeled with anti-red fluorescent protein (RFP) conjugated to biotin (ab34771, Abcam) (all diluted 1:100 in the blocking buffer). After 1 hour of incubation at room temperature in a humidity chamber, sections were washed three times in TBST and then incubated with phycoerythrin-conjugated streptavidin (554061, BD Biosciences) for 1 hour at room temperature. After washing, sections were incubated with DAPI for nuclear staining for 2 minutes at room temperature, then washed twice in TBST and once in water. Slides were air-dried at room temperature for 10 min, then mounted using Mowiol® 4-88 mounting medium. Images were captured using a KEYENCE BZ-X800 microscope (Keyence, Osaka, Osaka Prefecture, Japan). To create 3D reconstructions, images were captured using the confocal microscope ZEISS LSM 880 with Airyscan® (Oberkochen, Germany). Brightness, contrast, and smoothing were applied to the entire image using FIJI (open source). To determine the ratio of neutrophils to total cells, a total of five images per treatment (PBS, LPS, LPS+SR) and five regions of interest per image were used. The number of neutrophils divided by the total cell number was used to determine the neutrophil to total cell ratio.

Example 1-6. Immune Cell Isolation from Murine Fetal and Maternal Tissues

WT females were euthanized 24 hour post injection (E16, mouse embryonic day 16), and maternal (liver, lung, spleen, uterus or specifically uterus myometrium, cervix, decidua or specifically decidua basalis) and fetal (placenta, fetal membranes) tissues were collected cleaned to remove excess fat, then washed with cold PBS once. Isolation of immune cells from tissues was performed as previously described, but with modifications. Tissues were cut into small pieces using fine scissors, and they were enzymatically digested with Accutase® (Corning, Corning, N.Y.) for 35 minutes at 37° C. with gentle rocking. After incubation, the tubes were immediately placed on ice, then strained through a 70 μm cell strainer. Tissues were washed twice with 10.0 mL of 1×PBS, then centrifuged at 1250×g for 10 min at 4° C. Cell pellets were resuspended in 2.0 mL of RBC lysis buffer, incubated for 10 min at room temperature, and then centrifuged at 1250×g for 10 min at room temperature. Cell pellets were resuspended in 1.0 mL of serum-free Dulbecco's Modified Eagle Medium/Nutrient Mixture F-12 media (DMEM/F12; Mediatech Inc.) and mixed gently. Cell suspensions were gently overlaid on 500 μL of neat FBS (Sigma-Aldrich) in polystyrene plastic tubes, then centrifuged for 10 minutes at 1,100×g without the brake at room temperature. The supernatant was carefully aspirated, and the pellet was resuspended in 1.0 mL of DMEM/F12 supplemented with 10% FBS.

Example 1-7. Immunophenotyping of Fetal and Maternal Immune Cells

Neutrophil and Natural Killer (NK) Cells. To determine neutrophil and natural killer (NK) cell trafficking to fetal and maternal tissues, cells in DMEM/F12 with 10% FBS were centrifuged at 1250×g for 10 min at 4° C. Cell pellets were incubated with the CD16/CD32 antibody (101302, Biolegend, San Diego, Calif.) for 10 min, then incubated with zombie viability dye (BioLegend, San Diego, Calif.) and specific fluorophore-conjugated anti-mouse antibodies (Table 1) for 30 minutes at 4° C. in the dark. Cells were centrifuged at 600×g for 10 minutes, then run immediately on a Cytoflex® flow cytometer (Beckman Coulter, Brea, Calif.).

M1 and M2 Macrophages. To determine the macrophage phenotype and the trafficking to fetal and maternal tissues, cells were stimulated with phorbol 12-myristate 13-acetate (PMA, 50 ng/mL) and ionomycin (750 ng/mL) in the presence of GolgiStop® (BD Bioscience) in DMEM/F12 with 10% FBS and incubated at 37° C. in 5% $CO_2$ for 3 hours. After incubation, cells were collected and centrifuged at 2000×g for 10 minutes, then incubated with anti-CD16/CD32 and anti-F4/80, as described above. After centrifugation, cells were fixed and permeabilized, then stained with intracellular antibodies (Table 1) for 45 minutes at room temperature. Cells were centrifuged, then run immediately on the Cytoflex® flow cytometer (Beckman Coulter).

TABLE 1

| Antibodies used for immunophenotyping | | | |
|---|---|---|---|
| Antibody | Target Cell | Fluorophore | Catalog # (vendor) |
| CD16/32 | Fc Block | N/A | 101302 (Biolegend) |
| F4/80 | Macrophages | APC-R700 | 565787 (BD) |
| IL-1β | M1 Macrophages | FITC | IC4013F (Fisher) |
| TNF-α | M1 Macrophages | BB700 | 566510 (BD) |
| IL-10 | M2 Macrophages | APC | 554468 (BD) |
| IL-4 | M2 Macrophages | PE-Cy7 | 560699 (BD) |
| Ly6G | Neutrophils | FITC | 551460 (BD) |
| NK1.1 | NK cells | PerCP | 108726 (Biolegend) |
| DX5 | NK cells | AF 647 | 108912 (Biolegend) |
| Zombie (viability dye) | Non-viable cells | NIR | 423106 (Biolegend) |

Gating strategy for immunophenotyping of cells. Total leukocytes were identified using the forward scatter (cell size) and side scatter (cell granularity) parameters. After gating on viable cells, fetal cells by mT expression and maternal cells that were mT null were identified. Then, neutrophils by expression of Ly6G and NK cells by NK1.1 expression were identified. Mature NK cells were further identified by expression of DX5, which has been shown to indicate cells have increased cytotoxicity. Macrophages were identified using macrophage marker F4/80 and further characterized as pro-inflammatory, or M1 macrophages, with IL-1β+ and TNF-α+ expression and anti-inflammatory, or M2 macrophages with IL-10 and IL-4 expression.

Example 1-8. Statistical Analysis

Statistical analyses were performed using Prism 7 (GraphPad, San Diego, Calif.). All data are shown for n≥3 and displayed as the mean±standard error of the mean (SEM). Survival curves were generated using Prism 7. For preterm labor studies, statistical significance between groups was determined using a Kruskal-Wallis with a Benjamini-Hochberg post hoc test. For multiplex data and preterm labor studies, the statistical significance between groups was determined using a one-way ANOVA with a Tukey's post hoc test. For immunophenotyping of flow cytometry data, the statistical significance was determined using a two-way ANOVA with a Tukey correction for multiple analysis. A P value of ≤0.05 was considered significant.

A post hoc power analysis was performed using G*Power based on group means, standard deviation, and effect size (f=0.974 for Luminex analyses, 0.681 for maternal and fetal weight changes, 1.02 for preterm birth data and 1.56 for flow cytometry data). This analysis revealed that the study had ≥80% power for the ANOVA to detect differences between groups at a 0.05 significance level.

Example 2. Preparation of Exosomes Carrying Super Repressor IκB Protein (Exo-srIκB)

Exosomes were engineered to contain the NF-κB inhibitor using a technology called "EXPLOR" (EXosomes for Protein Loading via Optically Reversible protein—protein interactions) according to the method of Yim et al., a mutant form of IκBα that cannot be phosphorylated by IκB kinases and suppresses the translocation of the NF-κB complex to the nucleus, even in the presence of pro-inflammatory stimulation. FIG. 1A provides a schematic explanation of DNA constructs used to produce the srIκB (super repressor IκB)-loaded exosome (Exo-srIκB) (upper) and a schematic explanation showing fusion proteins and their proposed activities of light-dependent protein-protein interactions to create the Exo-srIκB (lower). Specifically, in the absence of light, pcDNA31(+) vector carrying CIBN-EGFP-CD9 gene and pcDNA31(+) vector carrying the super-repressor-IκB-mCherry-CRY2 gene were introduced into exosome-producing cell, HEK293T (human embryonic kidney) cells, and cultured for 24 hours. The transfected cells were washed with the culture media without fetal bovine serum (FBS) and grown for additional 48 hours. The cells then were irradiated with blue light of wavelength 488 nm.

Exosomes carrying SR (Exo-srIκB) as well as naïve exosomes (Exo-Naive) (isolated from non-transfected HEK293T cells) were characterized using TEM (FIG. 1B), where a characteristic cup-shaped morphology was found. Additionally, sizes and concentrations of exosomes were determined using NTA (FIG. 1C). Exo-srIκB and Exo-Naïve were between 30 and 150 nm in size, supporting the TEM data.

Example 3. Exosomes for Protein Loading Via Optically Reversible Protein—Protein Interactions (v) Technology to Engineer Exosomes to Contain NF-κB Inhibitor Protein, Super Repressor IκB To produce exosomes carrying srIκB, human embryonic kidney (HEK) 293T cells (CRL-3216, ATCC, Manassas, Va., USA) were stably transfected with constructs containing SR (FIG. 1A). For this, HEK293T cells stably expressing CIBN-EGFP-CD9 and srIκB-mcherry-CRY2 were established as described previously. For a detailed explanation of this method, please see work by Choi, et al. Briefly, under blue light illumination, exosomes containing srIκB (Exo-srIκB) were produced and then isolated using tangential flow filtration (TFF) and size exclusion chromatography (SEC). HEK293T cells were maintained in Dulbecco's modified Eagle's medium (DMEM) (Welgene, Seoul, Korea), containing 10% fetal bovine serum (FBS) (Gibco, Gaithersburg, Md., USA) and 1% penicillin—streptomycin (Gibco). HEK293T cells were transfected with pCMV-CIBN-EGFP and pCMV-srIκB-mCherry-CRY2 with the lipofectamine transfection reagent (Qiagen, Valencia, Calif., USA), according to the manufacturer's protocol. The cell population with high fluorescence intensity (green fluorescence protein, GFP, and mCherry) was measured, and then single-cell seeding on a 96-well plate was performed with a cell sorter (SH800 Cell Sorter, Sony, Minato, Tokyo, Japan). The best clone was chosen depending on the expression level of srIκB-mcherry-CRY2. The cell culture supernatant from SR-producing cells, as well as cells grown under standard conditions (naïve), were harvested and centrifuged at 1000 g for 15 minutes to remove cells and cell debris, then passed through a 0.22 µm polyethersulfone (PES) filter to remove any larger particles. The exosomes were isolated using molecular weight cutoff (MWCO)-based membrane filtration, and they were then purified by SEC chromatography.

Figure 1D:
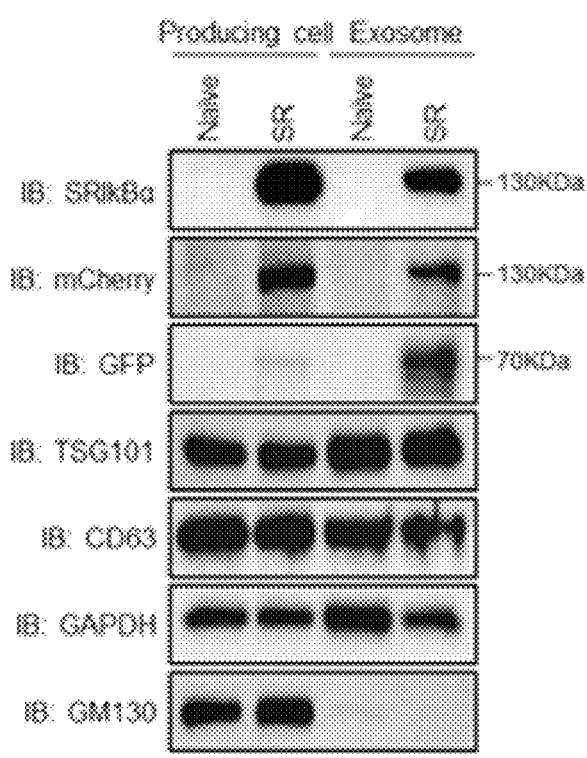

Western blots were performed to confirm packaging of SR in the exosomes, which was absent in naïve exosomes, as expected. Additional western blots were performed to show the presence of exosome markers TSG101 and CD63, as well as the absence of Golgi marker GM130 (FIG. 1D). HEK293T cells that stably express the super repressor (SR) IκB while naïve cells do not. Exosomes isolated from SR producing cells express SR, mCherry, GFP, as well as exosome markers TSG101 and CD63. Exosomes were negative for GM130. (FIG. 1D).

Example 4. SR Containing Exosomes Increased Lifespan of the Fetus in LPS-Induced Model After establishing that exosomes carry SR, it was tested if SR can increase lifespan of the fetus in mouse models. It was tested in a well-established CD-1 mouse model that consistently induces preterm labor within 12-14 hours to cause early termination of fetus.

Specifically, CD-1 mice (Charles River Laboratories, Huston, Tex.) of 15 days of pregnancy were intraperitoneally injected with LPS (100 μg) or PBS. After 30 minutes of injection, the mice were then administered with SR exosomes prepared in Example 1 (5)×10$^{10}$ or naive exosomes (HEK293T cell-derived exosomes, 5×10$^{10}$ via any of intraperitoneal (IP), intravenous (IV), intramuscular (IM) or subcutaneous (SubQ) routes 5 times at 2 hour intervals. Experimental groups are PBS: PBS injection; LPS: LPS+N IP: LPS+naive exosome intraperitoneal injection; LPS+SR IP: LPS+SR exosome intraperitoneal injection; LPS+SR IV: LPS+SR exosome intravenous injection; LPS+SR IM: LPS+SR exosome intraperitoneal injection; LPS+SR IV: LPS+SR exosome intravenous injection; LPS+SR IM: LPS+SR exosome intramuscular injection and; LPS+SR SubQ: or LPS+SR exosome subcutaneous injection.

Figure 2A:
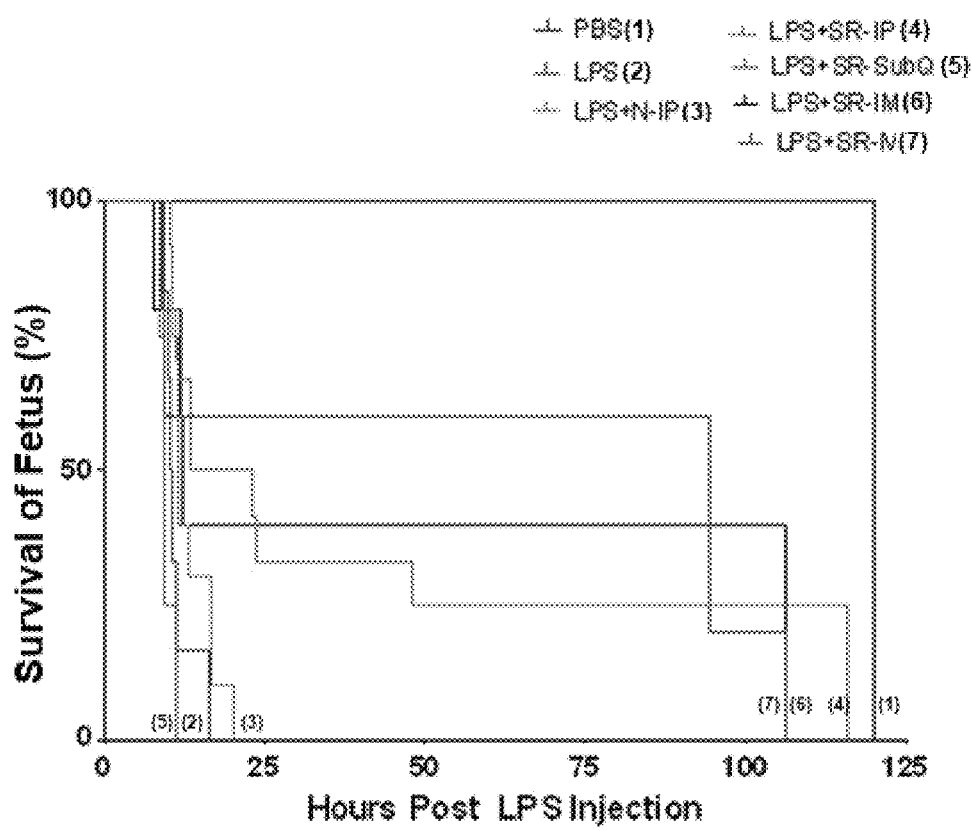
FIGS. 2A-2D shows the effect of Exo-srIkB on viability and weight of the pups (newborns). CD-1 mice of 15 weeks of pregnancy injected with LPS were injected Exo-srIκB.
Figure 2B:
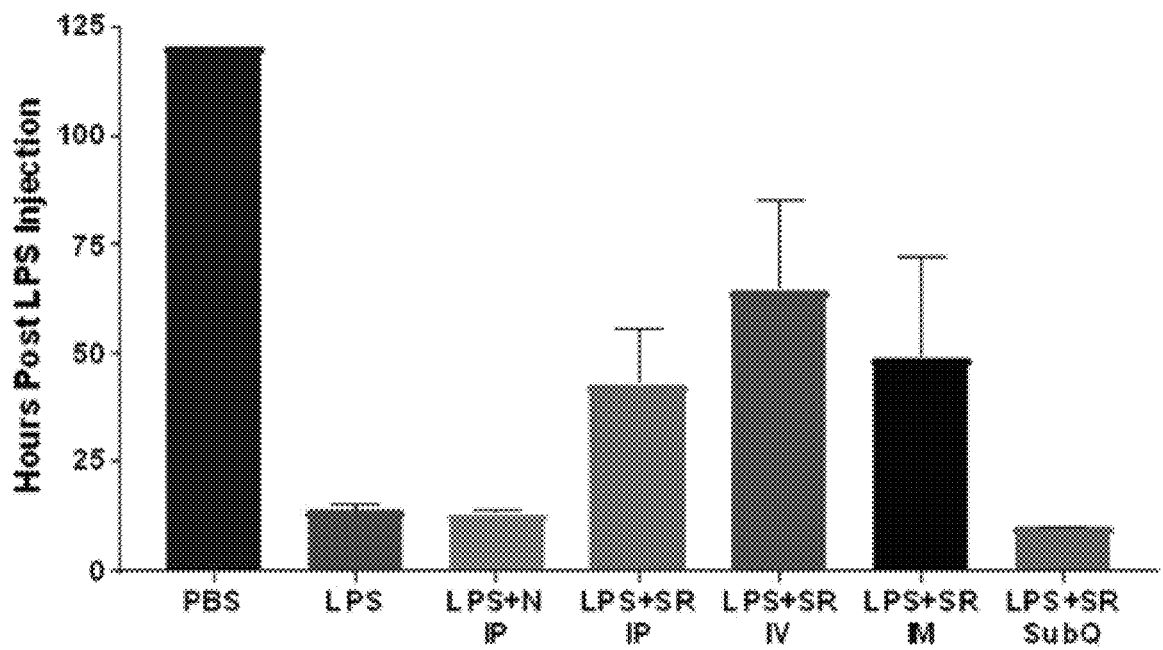

Mice injected with PBS maintained the full lifespan of the fetus (n=4, 112.5 hours post LPS, FIGS. 2A and 2B, Table 2), whereas all LPS mice terminated the lifespan of the fetus early (n=7, 11.5±0.929 hours post-LPS injection, P<0.0001 vs PBS).

TABLE 2

Increased lifespan of the fetus in CD-1 mice

| Group No. | Treatment$^a$ | N | Inhibition of early termination of fetus (%) | Average Lifespan of the fetus (Week) |
|---|---|---|---|---|
| 1 | PBS | 4 | NA | NA |
| 2 | LPS | 5 | 0 | 11.5 ± 0.929 |
| 3 | LPS + Naïve | 9 | 0 | 12.9 ± 1.06 |
| 4 | LPS + SR | 15 | 27 | 36 ± 10.2 |

$^a$PBS: control; LPS: LPS only; LPS + naïve: LPS with naïve exosomes without srIkB; LPS + SR: LPS with Exo-srIkB. NA: not applicable Naïve exosomes, exosome without srIkB, were used as controls for these experiments. Like LPS, all mice injected with LPS+naïve exosomes delivered preterm early terminating the fetus (n=11, 12.9±1.06 hours post LPS injection, P<0.0001 vs PBS, P=0.066 vs LPS+SR).

On the other hand, injection of Exo-srIkB, after LPS injection, increased lifespan of the fetus (n=16, 36±10.2 hours post LPS injection, P=0.0005 vs PBS, P=0.072 vs LPS) compared to the control group and lead to full term deliveries in about 27% of LPS+SR injected mice. The efficacy studies were performed using CD-1 mice, and all mechanistic studies were performed using a model in which C57BL/6J females are mated with mT homozygous males since this model carries the gene construct to examine fetal-specific cell trafficking. The result indicates that Exo-srIkB could increase lifespan and viability of the fetus. Between the different administration routes showed little difference in efficacy.

Figure 2C:
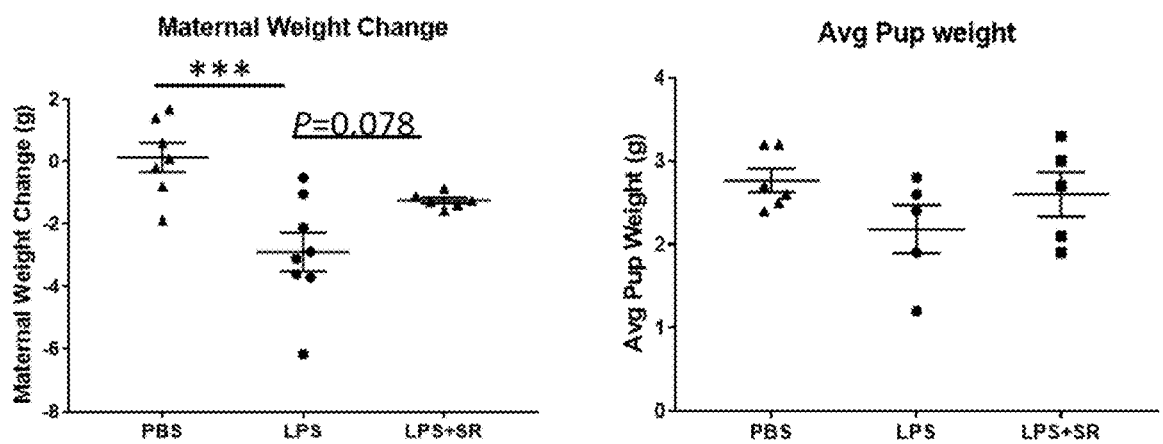
Figure 2D:
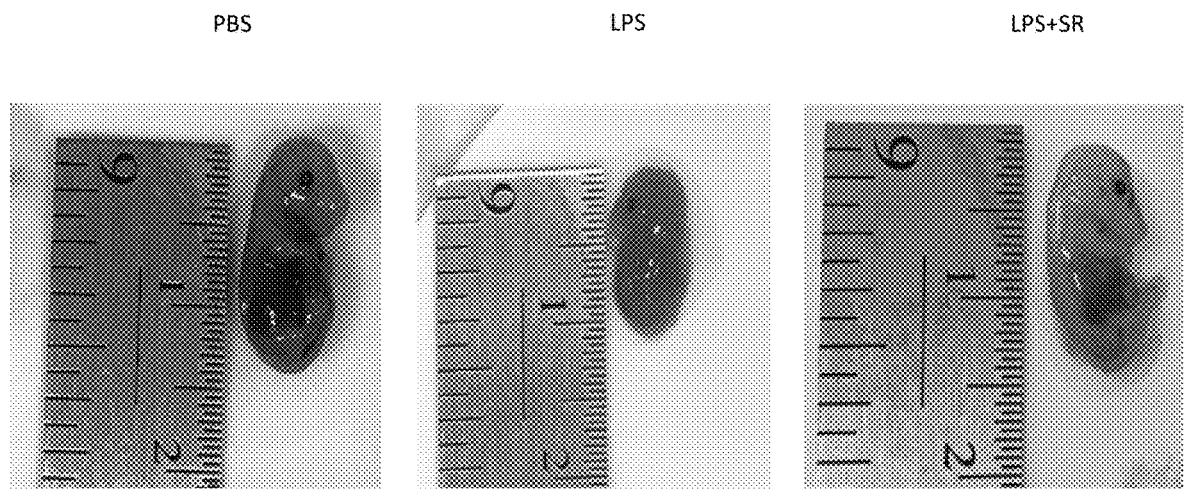

Twenty-four hours post LPS injection, mice were euthanized, and tissues were collected. LPS reduced maternal weight (−2.9±0.619 g, FIG. 2C, left), compared to PBS (0.12±0.469 g, P=0.0009). LPS+SR treatment (−1.25±0.098 g) increased the maternal weight to a significant level compared to LPS alone (P=0.078). The average pup weight and viability (based on fetal morphology and weight) were also improved with SR injection compared to LPS-injected mice (FIG. 2C, right and FIG. 2D).

Example 5. Expression of Inflammatory Cytokines and NF-κB Activation by Exosomes Containing Super-Repressor-IκB in Maternal Tissues Mice that delivered at least one pup, from each experimental group of Example 2 (PBS; LPS; LPS+Naive: LPS+naive exosome IP; and LPS+SR: LPS+SR exosome IP) were euthanized and maternal plasma, uterine and cervical tissues were collected. Then, the levels of pro-inflammatory cytokines IL-1β, IL-6 and IL-8 and anti-inflammatory cytokine IL-10 were measured using Luminex Multiple Assay (R&D System) according to the manufacturer's manual, and NF-κB activation by RelA phosphorylation (p-NF-κB) was analyzed.

As shown in FIGS. 3A-3D, the levels of proinflammatory cytokines IL-1β, IL-6 and IL-8 in the maternal plasma were lower in the LPS+SR exosome IP group compared to the LPS group. On the contrary, the level of the anti-inflammatory cytokine IL-10 was significantly higher than those in the mice from the LPS group (P=0.01) and PBS control group (P<0.0001).

Figure 3A:
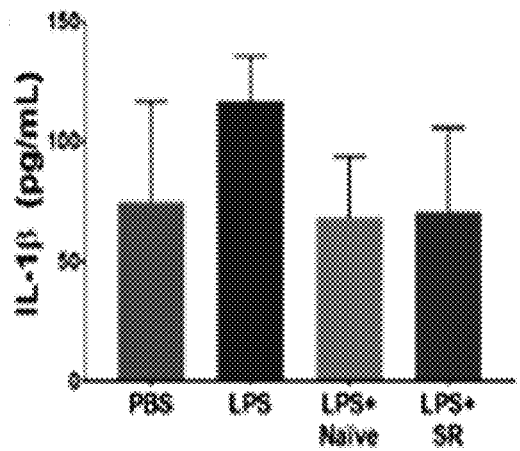
FIGS. 3A-3F shows the effect of the Exo-srIκB on the levels of the pro-inflammatory cytokines, IL-1β (FIG. 3A), IL-6 (FIG. 3B), and IL-8 (FIG. 3C), and anti-inflammatory cytokines IL-10 (FIG. 3D) in the cells isolated from the maternal plasma, and inflammatory transcription factor NF-kB in cervix (FIG. 3E), and in uterus (FIG. 3F) in LPS-injected CD-1 mice of 15 weeks of pregnancy, wherein the groups are as follows:
PBS: no LPS injection but only PBS injection;
LPS: LPS injection but no further treatment;
LPS+Naïve: LPS injection followed by treatment with Exo-Naïve; and
LPS+SR: LPS injection followed by treatment with Exo-srIκB.
Figure 3B:
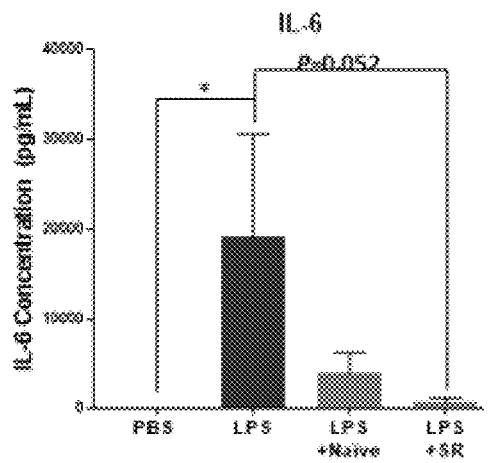
Figure 3C:
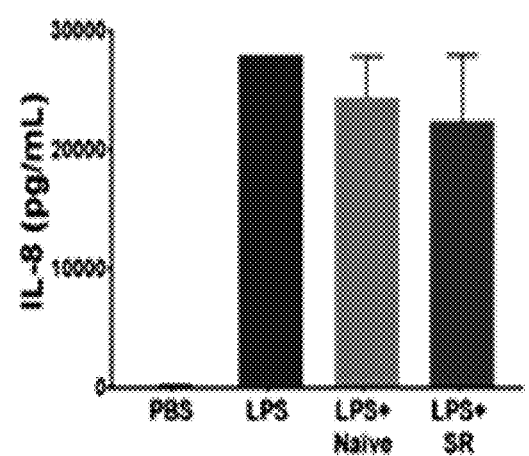
Figure 3D:
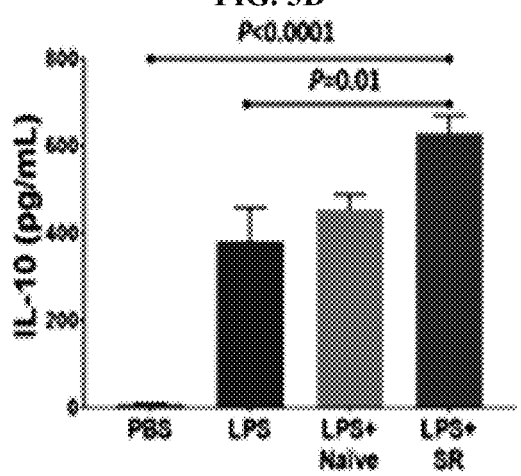
Figure 3E:
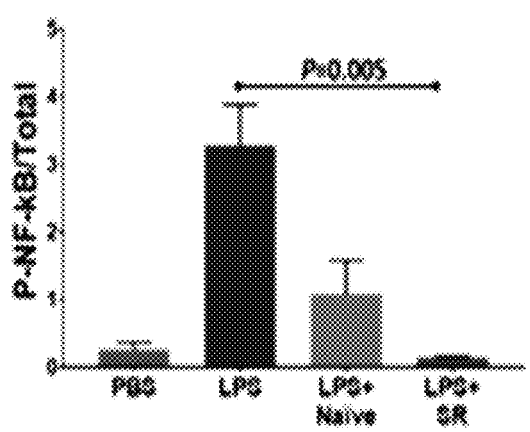
Figure 3F:
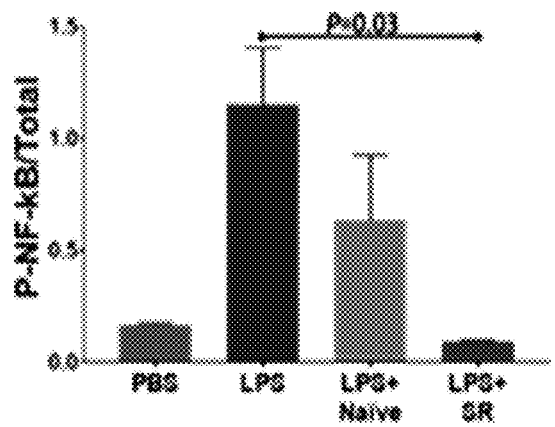

In addition, the effect of SR exosome on the expression of P—NF-κB in the maternal cervix and uterus was evaluated. The levels of P—NF-κB were much lower in The LPS+SR exosome IP group compared to the LPS group (P=0.005, P=0.03) (FIGS. 3E and 3F).

Figure 4:
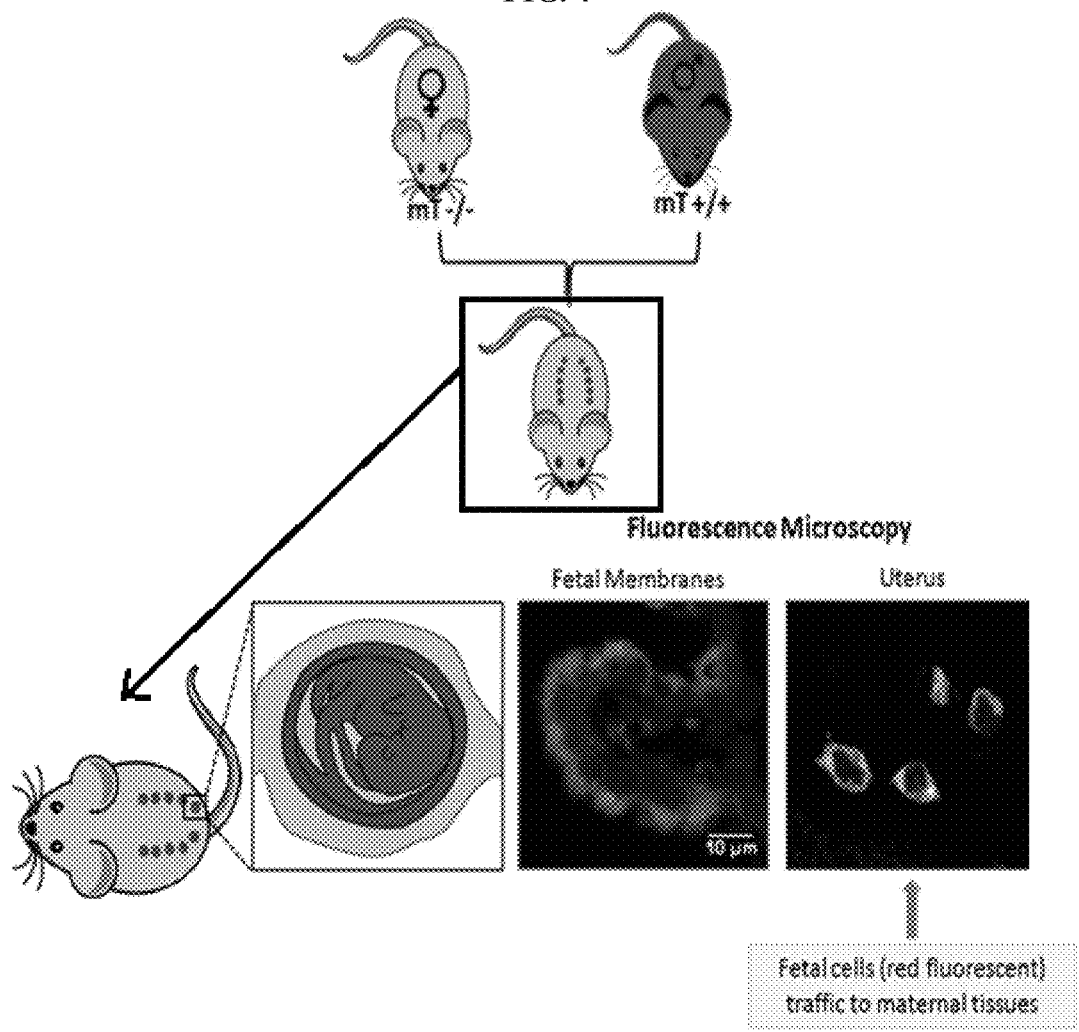
FIG. 4 shows a method for producing a transgenic animal model for fetal cell trafficking. To study fetal cell trafficking to maternal tissues, a mouse model that has a membrane-targeted tandem dimer Tomato (mT) red fluorescent protein expressed in all cells and tissues was developed. Female wild type (C57BL/6J) mice were mated with males homozygous to have all fetal, not any maternal, tissues expressing mT. The migration of fetal inflammatory cells in the maternal uterus were detected by a confocal microscope.
Figure 6A:
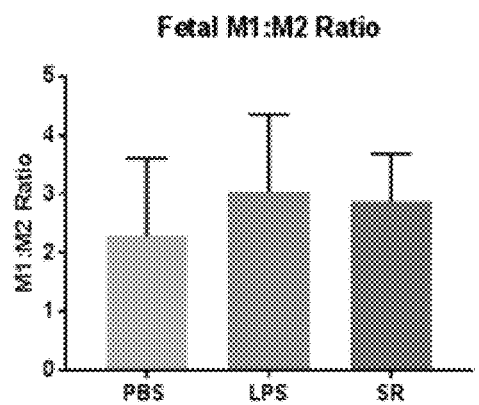
FIGS. 6A, 6B, 6C and 6D are graphs showing the effect of Exo-srIκB on migration and profile changes of the maternal and fetal inflammatory cells and pro-inflammatory fetal macrophage cells (M1) and anti-inflammatory fetal macrophage cells (M2). Mice of pregnancy model were injected with PBS, LPS and LPS+Exo-srIκB and profile change of inflammatory cells by Exo-srIκB were analyzed, wherein the groups are as follows:
PBS: no LPS injection but only PBS injection;
LPS: LPS injection but no further treatment; and
LPS+SR: LPS injection followed by treatment with Exo-srIκB.
Figure 6B:
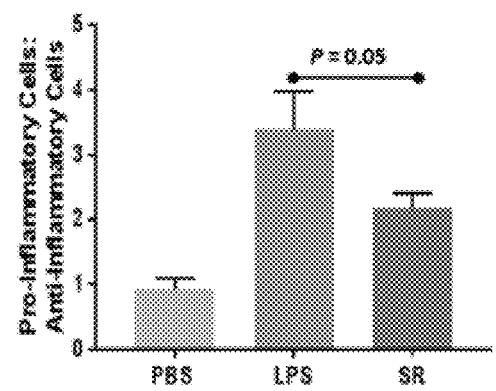
Figure 6C:
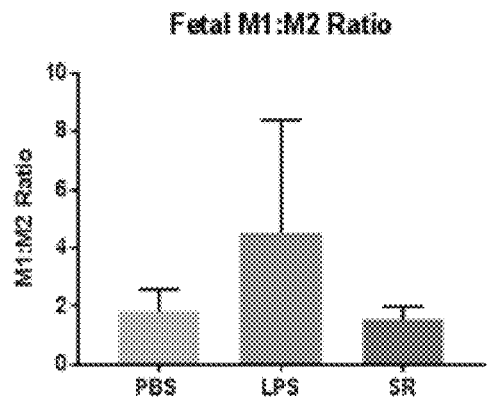
Figure 6D:
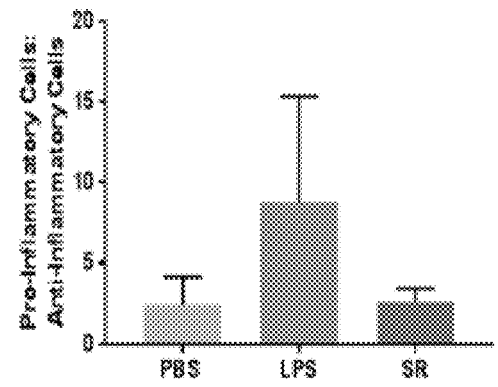

Example 6. Change in Inflammatory Profile of Fetal Inflammatory Cells by Exosomes Carrying Super-Repressor-IκB In order to determine if SR exosome can delay preterm labor, the migration of fetal inflammatory cells to the maternal uterus and changes in the inflammatory profile of fetal inflammatory cells were analyzed.

tdTomato homozygous male C57BL/6J mice (Jackson Laboratory) expressing a red fluorescent protein in all cells and tissues, and wild-type female C57BL/6J mice (Jackson Laboratory) were crossed to allow tdTomato to be expressed in all fetal tissues. Then, using a confocal microscope, it is confirmed that fetal inflammatory cells were founded in the fetal membrane of the female mouse at the 15 days of pregnancy (FIG. 4). The uterine tissues and fetal membranes were removed and the fluorescent maternal cells and red fluorescent fetal cells were isolated to analyze for pro-inflammatory IL-1β and TNF-α, and anti-inflammatory IL-10 by flow cytometry as shown in the schematic diagram of FIG. 5. In addition, fetal macrophages (mT+) were analyzed using the macrophage marker F4/80. Flow cytometric analysis confirms that the fetal inflammatory cells migrate to the maternal uterus.

The female mice of 15 days of pregnancy were injected with LPS or PBS as described in Example 2, and SR exosomes were administered intraperitoneally 5 times at 2 hour intervals after 24 hours post-injection with LPS. Uterine and fetal membrane tissues were collected from PBS, LPS and SR (LPS+SR exosome) mice groups. Following the method as described above, the ratios of pro-inflammatory M1 macrophages and anti-inflammatory M2 macrophages and the ratio of fetal pro-inflammatory cells and anti-inflammatory cells in the uterus and fetal membrane were evaluated were analyzed (FIG. 6A-6D).

As shown in FIG. 6A-6D, the M1:M2 ratios of fetal macrophages in the uterus decreased by administration of SR exosomes and the ratio of fetal pro-inflammatory cells: anti-inflammatory cells were also significantly reduced in the uterus. In addition, it was confirmed that the fetal macrophage M1:M2 ratios and the pro-inflammatory cell: anti-inflammatory cell ratios decreased similarly to those of the maternal uterus by the SR exosome treatment in the fetal membrane.

Example 7. SR Exosome Treatment Reduces Neutrophil Infiltration and Histologic Chorioamnionitis (HCA)

Histologic chorioamnionitis (HCA) is defined by the presence of polymorphonuclear leukocyte infiltration of the fetal membranes, and these cells are thought to be primarily of maternal origin. HCA is an indicator of inflammation, and it can determine pregnancy outcomes as well as indicate neonatal morbidities. Using fluorescence microscopy, the mT expressing fetal membranes of mice injected with PBS (FIG. 7A), LPS (FIG. 7B), and LPS+SR (FIG. 7C) were stained for neutrophils by the expression of mouse lymphocyte antigen 6 complex locus G6D (Ly6G). LPS-injected animals (0.282±0.043) had increased ratios of Ly6G+ cells to total cells in the fetal membranes (FIG. 7D), compared to either PBS (0.119±0.045, P=0.008) or LPS+SR (0.100±0.032, P=0.001).

Figure 8A:
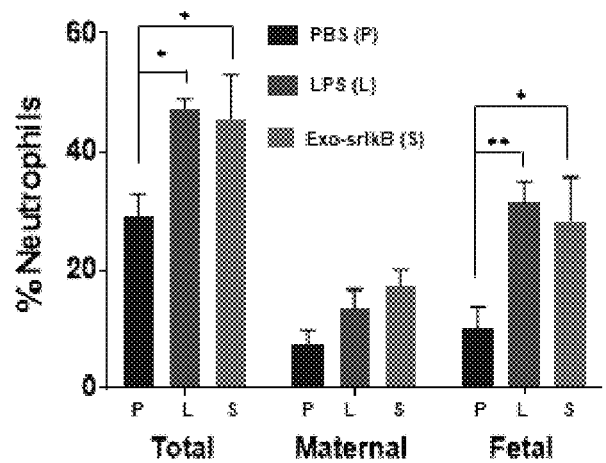
FIGS. 8A-8E show flow cytometry analysis of fetal and maternal neutrophils and natural killer (NK) cells of PBS-, LPS- and LPS+Exo-srIκB-injected groups of mice.
Figure 8B:
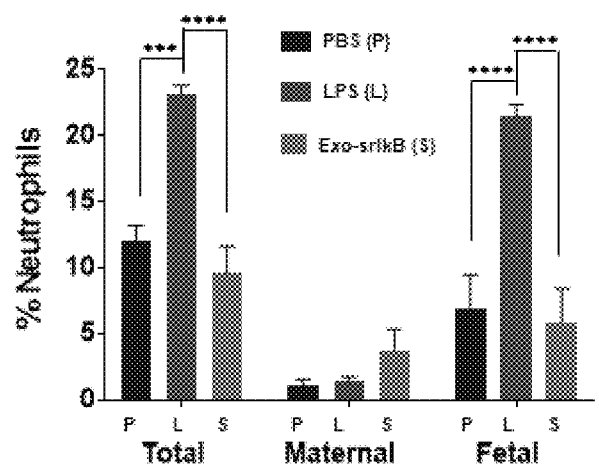

Example 8. Increase in Fetal Neutrophil Infiltration in Fetal Tissues after LPS Challenge is Reduced with SR To identify whether immune cells were fetal or maternal, after gating on viable cells, mT+fetal cells were identified by red fluorescence, whereas maternal cells were negative. After identifying fetal and maternal cells, neutrophils (Ly6G+ cells) were identified and counted. In the placenta, compared to PBS, mice injected with LPS had significantly increased total (mT− and mT+, P=0.03) and mT+Ly6G+ cells (LPS, P=0.006) (FIG. 8A). Similarly, compared to PBS, LPS+SR had significantly increased total (P=0.050) and mT+Ly6G+ cells (P=0.018). In the fetal membranes, LPS-injected mice had significantly higher total (P=0.0005) and mT+Ly6G+(P<0.0001) cells than PBS. Compared to LPS, LPS+SR had significantly lower total and mT+Ly6G+ cells (all P<0.0001), indicating that treatment with SR may reduce HCA (FIG. 8B). This supports the data shown in FIGS. 7A-7C.

Figure 8C:
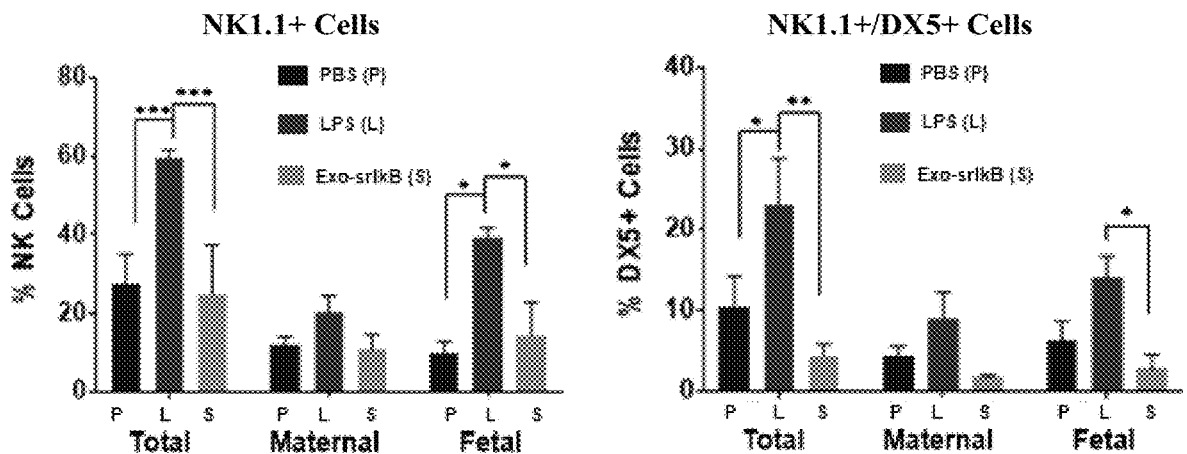
Figure 8D:
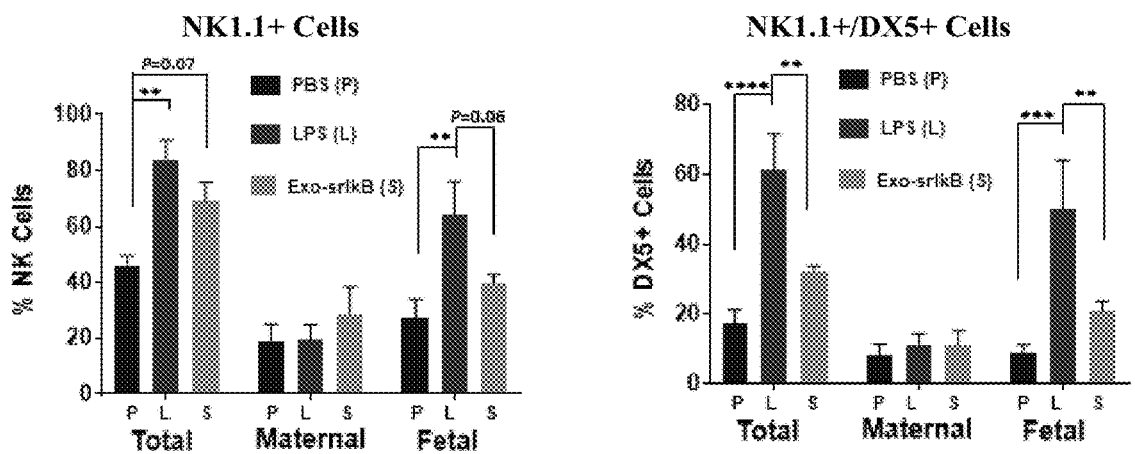
Figure 8E:
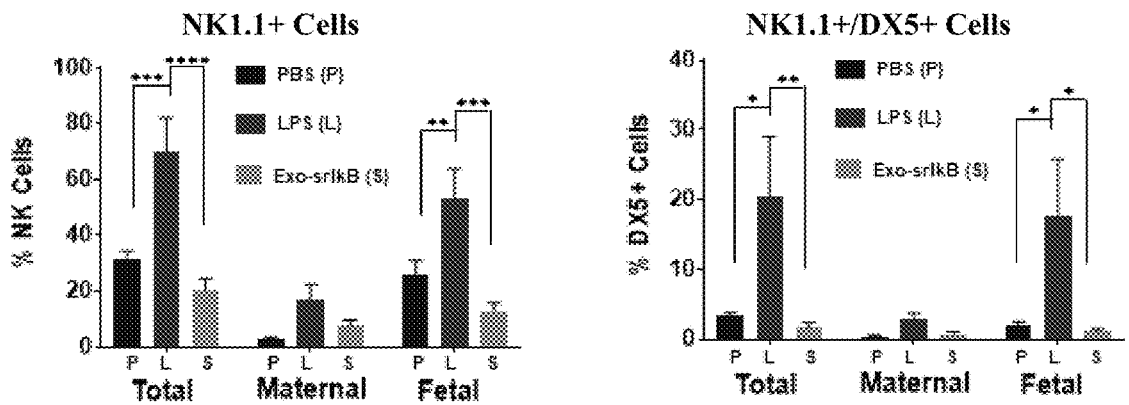

Example 9. The Cytotoxic NK Cell Response to LPS Challenge in Fetal and Maternal Tissues is Primarily Fetal in Origin and is Reduced with SR Treatment To test whether these infiltrated NK cells are fetal or maternal in origin, fetal NK cells as mT+/NK1.1+(also known as CD161b/CD161 in mouse) cells were determined. Furthermore, we determined maturity of NK cells by the presence of DX5, also known as CD49b or a2 integrin, very late antigen-2, which denotes the transition of NK cells to a mature phenotype and has been associated with an increased cytotoxicity. In the uterus and decidua, no changes were seen in the percentages of NK1.1+ cell and NK1.1+/DX5+NK cells. However, in the cervix, compared to PBS, LPS significantly increased the percentage of total (P=0.003), mT+/NK1.1+(P=0.011) cells, and mT+/NK1.1+/DX5+ cells (P=0.014, FIG. 8C). With SR treatment, compared to LPS, total NK1.1+(P=0.003), mT+/NK1.1+(P=0.032), total NK1.1+/DX5+(P=0.001), and mT+/NK1.1+/DX5+ (P=0.045) cells were significantly decreased (FIG. 8C). In the placenta, there was a significant increase in total NK1.1+ cells in PBS mice compared to LPS-injected mice (P=0.002) and a significant reduction in total NK1.1+ cells after SR treatment (P=0.065, FIG. 8D). Total NK1.1+/DX5+ cells and mT+/NK1.1+/DX5+ cells in the placenta of LPS-injected mice were increased compared to PBS (all P<0.0001). Treatment with SR reduced total NK1.1+/DX5+(P=0.009) and mT+/NK1.1+/DX5+ cells (P=0.008, FIG. 8D); however, no changes were seen in maternal NK1.1+/DX5+ cells. In the fetal membranes, total NK1.1+(P=0.0003) and mT+/NK1.1+(P=0.008) cells, as well as total NK1.1+/DX5+ (P=0.016) and mT+/NK1.1+/DX5+(P=0.017) cells, were increased after LPS injection compared to PBS. Compared to LPS, total NK1.1+(P<0.0001) and mT+/NK1.1+ cells (P=0.0004), as well as total NK1.1+/DX5+(P=0.008) and mT+/NK1.1+/DX5+(P=0.018) cells, were significantly reduced after treatment with SR (FIG. 8E). These results indicate that the predominant NK cell response to LPS challenge is of fetal, not maternal, origin and this was reduced with SR in both fetal and maternal tissues.

Example 10. Fetal Macrophages are Localized in Maternal Tissues

To test our hypothesis that fetal innate immune cells, along with maternal immune cells, can traffic to both fetal and maternal tissues, we utilized an established transgenic mouse model that differentiates between fetal and maternal cells. To determine fetal innate immune cell trafficking to the maternal compartment, we collected uterus, cervix, and decidua and colocalized mT+ expressing cells with F4/80, a murine macrophage marker. As shown in FIGS. 9A-9C, using confocal microscopy, mT+(red fluorescence) and F4/80+(green fluorescence) macrophages were colocalized in all maternal uterine tissues tested.

Example 11. LPS-Induced Immune Cell Infiltration Seen in Preterm Birth in a Mouse Model is Predominantly a Fetal Response and is Reduced at the Feto-Maternal Interface with SR Exosome Treatment PTB in CD-1 mouse model can be delayed using NF-κB inhibitory drugs packaged into exosomes. This delay is associated with a reduction in fetal immune cell trafficking in placenta, fetal membranes and cervix.

The results by LPS: Comparison between LPS and PBS (FIG. 10, left) shows that:
Cervix: LPS injected mice had increased total NK1.1+ and DX5+NK cells, and increased fetal NK1.1+ cells.
Uterus: LPS injected mice had increased total and maternal M1 and M2 Macrophages.
Decidua: LPS injected mice had increased total neutrophils and decreased total M1 and M2 Macrophages, as well as decreased maternal M2 Macrophages.
Placenta: LPS injected mice had increased total neutrophils, NK cells and DX5+NK cells. Additionally, fetal neutrophils, NK cells and DX5+NK cells were also increased in LPS-injected mice.
Fetal membranes: LPS-injected mice had increased total and fetal neutrophils, increased total and fetal NK cells and increased total and fetal DX5+NK cells.

Arrows indicate increase or decrease in number of cells.
*P=0.07.

Comparison between LPS and LPS+SR (FIG. 10, right) shows that:

Cervix: LPS+SR had decreased total and fetal NK cells and DX5+NK cells.

Uterus: LPS+SR had decreased total M1 and M2 Macrophages and decreased maternal M2 Macrophages.

Decidua: No changes were seen in the decidua with SR treatment.

Placenta: LPS+SR had decreased total DX5+NK cells, as well as decreased fetal NK cells and DX5+NK cells.

Fetal membranes: LPS+SR-injected mice had decreased total and fetal neutrophils, decreased total and fetal NK cells and decreased total and fetal DX5+NK cells.

Arrows indicate increase or decrease in number of cells.
**P=0.06.

The experimental results indicate that the fetal inflammatory response primes maternal uterine tissues to transition them to a parturition phenotype. This inflammatory response could be in response to a risk factor in PTB (e.g., infection), fetal tissue senescence, or signals of organ maturation capable of creating NF-κB activation in the fetal membranes and placenta.

Maternal administration of engineered exosomes containing anti-inflammatory NF-κB molecules reduced fetal inflammatory response, fetal innate immune cell migration, histologic chorioamnionitis and delayed preterm delivery in a mouse model of infection.

The result indicate that the infiltration of the exosomes containing anti-inflammatory NF-κB molecules will improve viability of the fetus and the health of the newborn.

Example 12. The Combined Treatment of SR Exosome with an Antibiotic or a Uterine Contraction Inhibitor in an Inflammation Caused by Infection A synergistic effect of combined treatment of SR exosome with an antibiotic or a uterine contraction inhibitor for treating inflammation caused by infection is studied and is found that the combined treatment of the infected model significantly reduces inflammation caused by infection with E. coli, improved viability of the fetus, and delays the live bacteria-induced preterm birth.

At least 40% of preterm births are associated with intrauterine infection. Current animal models for preterm labor typically use lipopolysaccharide (LPS) that is intraperitoneally injected into pregnant mice to induce a systemic inflammation, rather than a localized inflammation typically associated with intrauterine infection. A clinically relevant model of a preterm labor in a mouse was established using live bacteria (i.e. E. coli) and administered it either vaginally to mimic ascending infection or intra-uterine injection to mimic the highly localized inflammation associated with infection-induced preterm birth (FIGS. 11A and 11B).

To determine the synergistic efficacy of SR exosome with Gentamycin (an antibiotic) or Indomethacin (a tocolytic agent, or a uterine contraction inhibitor) in E. coli-induced preterm birth, CD-1 pregnant mice are administered with optimal dose of SR exosome combined with Gentamycin or Indomethacin, and are monitored for survival rate and delayed preterm birth. Survival rate of mice and the viability of the pups (newborns) are measured in E. coli-injected CD-1 pregnant mice groups injected with PBS, Gentamycin (5-150 mg/kg), Indomethacin (1-50 mg/kg), Exo-srIkB once, three or five times with different doses (1E+9~1E+11), Exo-srIkB+Gentamycin, Exo-srIkB+Indomethacin.

The invention claimed is:

1. A method for increasing lifespan of fetus, viability of fetus, or viability of newborn, for treating inflammation in uterus fetus, for delaying preterm birth, or for treating a condition related to inflammation in uterus and/or fetus during pregnancy comprising:
administering a composition comprising extracellular vesicles comprising a nuclear factor kappa beta (NF-κB) inhibitor to a subject in need thereof.

2. The method of claim 1, wherein the extracellular vesicles are exosomes.

3. The method of claim 1, wherein the composition comprises a photo-specific binding protein, and the photo-specific binding protein is a first photo-specific binding protein or a second photo-specific binding protein.

4. The method of claim 3, wherein the first photo-specific binding protein is conjugated to an exosome specific marker to form a first fusion protein (fusion protein I); and the second photo-specific binding protein is conjugated to the NF-κB inhibitory protein to form a second fusion protein (fusion protein II).

5. The method of claim 4, wherein the fusion protein I and the fusion protein II are linked reversibly through the first photo-specific binding protein and the second photo-specific binding protein.

6. The method of claim 4, wherein the first photo-specific binding protein is conjugated to the exosome specific marker to be located in the direction toward inside of the exosome.

7. The method of claim 3, wherein the first photo-specific binding protein and the second photo-specific binding protein are selected from the group consisting of cryptochrome-interacting basic-helix-loop-helix protein (CIB), N terminal domain of CIB (CIBN), phytochrome B (PhyB), phytochrome interacting factor (PIF), Flavin binding, Kelch repeat F-box 1 (FKF1), GIGANTEA, CRY2 cryptochrome 2 (CRY2) and photolyase-homologous region (PHR).

8. The method of claim 3, wherein the first photo-specific binding protein is CIB or CIBN and the second photo-specific binding protein is CRY2 or PHR, or the first photo-specific binding protein is CRY2 or PHR and the second photo-specific binding protein is CIB or CIBN.

9. The method of claim 3, wherein the first photo-specific binding protein is PhyB and the second photo-specific binding protein is PIF or the first photo-specific binding protein is PIF and the second photo-specific binding protein is PhyB.

10. The method of claim 3, wherein the first photo-specific binding protein is GIGANTEA and the second photo-specific binding protein is FKF1 or the first photo-specific binding protein is FKF1 and the second photo-specific binding protein is GIGANTEA.

11. The method of claim 4, wherein the exosome specific marker is selected from the group consisting of CD9, CD63, CD81 and CD82.

12. The method of claim 1, wherein the NF-κB inhibitor is selected from the group consisting of a NF-κB inhibiting drug, a NF-κB inhibitory protein or fragment thereof, and a mixture thereof.

13. The method of claim 1, wherein the NF-κB inhibitory protein is selected from the group consisting of IκB, super repressor-IκB (srIκB), IκB-α, IκB-β, IκB-ε and B cell lymphoma 3 (BCL3), a mutant thereof and a mixture thereof.

14. The method of claim 1, wherein the composition is administered via oral, transdermal, intraperitoneal, intravenous, intramuscular, subcutaneous, intradermal, vaginal, intrauterine route, or a mixture thereof.

15. The method of claim 1, further comprising:
administering an antibiotic or a uterine contraction inhibitor with, before or after the administration of the composition of claim 1.

16. The method of claim 15, wherein the antibiotic is selected from the group consisting of penicillin, cephalosporins, macrolides, lincosamide, carbapenems, glycopeptides, aminoglycosides, tetracyclines, erythromycin, nitroimidazoles, β-lactamase inhibitors, a derivative thereof, and a mixture thereof; and the uterine contraction inhibitor is selected from the group consisting of progesterone, nifedipine, atosiban, ritodrine, indomethacin, magnesium sulfate, orciprenaline, terbutaline, salbutamol, fenoterol, nylidrin, isoxsuprine, hexoprenaline, and a mixture thereof.

17. The method of claim 1, wherein the condition related to inflammation in uterus and/or fetus during pregnancy is selected from the group consisting of prenatal inflammatory response, prenatal labor, preterm delivery, preterm rupture of amniotic membrane, low birth weight, adenomyosis, fetal inflammatory response syndrome (FIRS), uterine fibroid, intrauterine inflammation, chorioamnionitis, amnionitis, amniotic fluid infection, placental infection, and intraamniotic infection (Intra-amniotic infection), and a mixture thereof.

18. The method of claim 17, wherein the condition related to inflammation in uterus and/or fetus during pregnancy is selected from the group consisting of prenatal inflammatory response, prenatal labor, preterm delivery, preterm rupture of amniotic membrane, low birth weight, adenomyosis, fetal inflammatory response syndrome (FIRS), uterine fibroid, and a mixture thereof.

19. The method of claim 1, wherein the NF-κB inhibitor comprises a super repressor-IκB(srIκB).

20. A method of changing inflammatory profile of fetal inflammatory cells or fetal inflammatory cell migration comprising: administering a composition comprising extracellular vesicles comprising a nuclear factor kappa beta (NF-κB) inhibitor to a subject in need thereof.

21. The method of claim 20, wherein the NF-κB inhibitor comprises a super repressor-IκB(srIκB).

* * * * *

SEQUENCE LISTING

```
<160> NUMBER OF SEQ ID NOS: 8

<210> SEQ ID NO 1
<211> LENGTH: 317
<212> TYPE: PRT
<213> ORGANISM: Homo sapiens

<400> SEQUENCE: 1

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ala
            20                  25                  30

Gly Leu Asp Ala Met Lys Asp Glu Glu Tyr Glu Gln Met Val Lys Glu
        35                  40                  45

Leu Gln Glu Ile Arg Leu Glu Pro Gln Glu Val Pro Arg Gly Ser Glu
    50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
    130                 135                 140
```

-continued

```
Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Leu Gly Gln Leu
            260                 265                 270

Thr Leu Glu Asn Leu Gln Met Leu Pro Glu Ser Glu Asp Glu Glu Ser
        275                 280                 285

Tyr Asp Thr Glu Ser Glu Phe Thr Glu Phe Thr Glu Asp Glu Leu Pro
    290                 295                 300

Tyr Asp Asp Cys Val Phe Gly Gly Gln Arg Leu Thr Leu
305                 310                 315
```

<210> SEQ ID NO 2
<211> LENGTH: 317
<212> TYPE: PRT
<213> ORGANISM: Homo sapiens

<400> SEQUENCE: 2

```
Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
            20                  25                  30

Gly Leu Asp Ser Met Lys Asp Glu Glu Tyr Glu Gln Met Val Lys Glu
        35                  40                  45

Leu Gln Glu Ile Arg Leu Glu Pro Gln Glu Val Pro Arg Gly Ser Glu
    50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
```

```
            195                 200                 205
Val Asn Ala Gln Glu Pro Cys Asn Gly Arg Thr Ala Leu His Leu Ala
210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
                275                 280                 285

Tyr Asp Thr Glu Ser Glu Phe Thr Glu Phe Thr Glu Asp Glu Leu Pro
290                 295                 300

Tyr Asp Asp Cys Val Phe Gly Gly Gln Arg Leu Thr Leu
305                 310                 315

<210> SEQ ID NO 3
<211> LENGTH: 356
<212> TYPE: PRT
<213> ORGANISM: Homo sapiens

<400> SEQUENCE: 3

Met Ala Gly Val Ala Cys Leu Gly Lys Ala Ala Asp Ala Asp Glu Trp
1               5                   10                  15

Cys Asp Ser Gly Leu Gly Ser Leu Gly Pro Asp Ala Ala Pro Gly
                20                  25                  30

Gly Pro Gly Leu Gly Ala Glu Leu Gly Pro Gly Leu Ser Trp Ala Pro
            35                  40                  45

Leu Val Phe Gly Tyr Val Thr Glu Asp Gly Asp Thr Ala Leu His Leu
50                  55                  60

Ala Val Ile His Gln His Glu Pro Phe Leu Asp Phe Leu Leu Gly Phe
65                  70                  75                  80

Ser Ala Gly Thr Glu Tyr Met Asp Leu Gln Asn Asp Leu Gly Gln Thr
                85                  90                  95

Ala Leu His Leu Ala Ala Ile Leu Gly Glu Thr Ser Thr Val Glu Lys
                100                 105                 110

Leu Tyr Ala Ala Gly Ala Gly Leu Cys Val Ala Glu Arg Arg Gly His
            115                 120                 125

Thr Ala Leu His Leu Ala Cys Arg Val Gly Ala His Ala Cys Ala Arg
130                 135                 140

Ala Leu Leu Gln Pro Arg Pro Arg Arg Pro Arg Glu Ala Pro Asp Thr
145                 150                 155                 160

Tyr Leu Ala Gln Gly Pro Asp Arg Thr Pro Asp Thr Asn His Thr Pro
                165                 170                 175

Val Ala Leu Tyr Pro Asp Ser Asp Leu Glu Lys Glu Glu Glu Ser
                180                 185                 190

Glu Glu Asp Trp Lys Leu Gln Leu Glu Ala Glu Asn Tyr Glu Gly His
            195                 200                 205

Thr Pro Leu His Val Ala Val Ile His Lys Asp Val Glu Met Val Arg
210                 215                 220

Leu Leu Arg Asp Ala Gly Ala Asp Leu Asp Lys Pro Glu Pro Thr Cys
225                 230                 235                 240

Gly Arg Ser Pro Leu His Leu Ala Val Glu Ala Gln Ala Ala Asp Val
                245                 250                 255
```

```
Leu Glu Leu Leu Leu Arg Ala Gly Ala Asn Pro Ala Ala Arg Met Tyr
                260                 265                 270

Gly Gly Arg Thr Pro Leu Gly Ser Ala Met Leu Arg Pro Asn Pro Ile
            275                 280                 285

Leu Ala Arg Leu Leu Arg Ala His Gly Ala Pro Glu Pro Glu Gly Glu
        290                 295                 300

Asp Glu Lys Ser Gly Pro Cys Ser Ser Ser Asp Ser Asp Ser Gly
305                 310                 315                 320

Asp Glu Gly Asp Glu Tyr Asp Asp Ile Val Val His Ser Ser Arg Ser
                325                 330                 335

Gln Thr Arg Leu Pro Pro Thr Pro Ala Ser Lys Pro Leu Pro Asp Asp
            340                 345                 350

Pro Arg Pro Val
        355

<210> SEQ ID NO 4
<211> LENGTH: 270
<212> TYPE: PRT
<213> ORGANISM: Homo sapiens

<400> SEQUENCE: 4

Met Asp Leu Gln Asn Asp Leu Gly Gln Thr Ala Leu His Leu Ala Ala
1               5                   10                  15

Ile Leu Gly Glu Thr Ser Thr Val Glu Lys Leu Tyr Ala Ala Gly Ala
            20                  25                  30

Gly Leu Cys Val Ala Glu Arg Gly His Thr Ala Leu His Leu Ala
        35                  40                  45

Cys Arg Val Gly Ala His Ala Cys Ala Arg Ala Leu Leu Gln Pro Arg
    50                  55                  60

Pro Arg Arg Pro Arg Glu Ala Pro Asp Thr Tyr Leu Ala Gln Gly Pro
65                  70                  75                  80

Asp Arg Thr Pro Asp Thr Asn His Thr Pro Val Ala Leu Tyr Pro Asp
                85                  90                  95

Ser Asp Leu Glu Lys Glu Glu Glu Ser Glu Glu Asp Trp Lys Leu
            100                 105                 110

Gln Leu Glu Ala Glu Asn Tyr Glu Gly His Thr Pro Leu His Val Ala
        115                 120                 125

Val Ile His Lys Asp Val Glu Met Val Arg Leu Leu Arg Asp Ala Gly
    130                 135                 140

Ala Asp Leu Asp Lys Pro Glu Pro Thr Cys Gly Arg Ser Pro Leu His
145                 150                 155                 160

Leu Ala Val Glu Ala Gln Ala Ala Asp Val Leu Glu Leu Leu Leu Arg
                165                 170                 175

Ala Gly Ala Asn Pro Ala Ala Arg Met Tyr Gly Gly Arg Thr Pro Leu
            180                 185                 190

Gly Ser Ala Met Leu Arg Pro Asn Pro Ile Leu Ala Arg Leu Arg
        195                 200                 205

Ala His Gly Ala Pro Glu Pro Glu Gly Glu Asp Glu Lys Ser Gly Pro
    210                 215                 220

Cys Ser Ser Ser Asp Ser Asp Ser Gly Asp Glu Gly Asp Glu Tyr
225                 230                 235                 240

Asp Asp Ile Val Val His Ser Ser Arg Ser Gln Thr Arg Leu Pro Pro
                245                 250                 255

Thr Pro Ala Ser Lys Pro Leu Pro Asp Asp Pro Arg Pro Val
            260                 265                 270
```

<210> SEQ ID NO 5
<211> LENGTH: 338
<212> TYPE: PRT
<213> ORGANISM: Homo sapiens

<400> SEQUENCE: 5

Met Ala Gly Val Ala Cys Leu Gly Lys Ala Ala Asp Ala Asp Glu Trp
1               5                   10                  15

Cys Asp Ser Gly Leu Gly Ser Leu Gly Pro Asp Ala Ala Pro Gly
            20                  25                  30

Gly Pro Gly Leu Gly Ala Glu Leu Gly Pro Gly Leu Ser Trp Ala Pro
            35                  40                  45

Leu Val Phe Gly Tyr Val Thr Glu Asp Gly Asp Thr Ala Leu His Leu
    50                  55                  60

Ala Val Ile His Gln His Glu Pro Phe Leu Asp Phe Leu Leu Gly Phe
65                  70                  75                  80

Ser Ala Gly Thr Glu Tyr Met Asp Leu Gln Asn Asp Leu Gly Gln Thr
                85                  90                  95

Ala Leu His Leu Ala Ala Ile Leu Gly Glu Thr Ser Thr Val Glu Lys
            100                 105                 110

Leu Tyr Ala Ala Gly Ala Gly Leu Cys Val Ala Glu Arg Arg Gly His
        115                 120                 125

Thr Ala Leu His Leu Ala Cys Arg Val Gly Ala His Ala Cys Ala Arg
130                 135                 140

Ala Leu Leu Gln Pro Arg Pro Arg Arg Pro Arg Glu Ala Pro Asp Thr
145                 150                 155                 160

Tyr Leu Ala Gln Gly Pro Asp Arg Thr Pro Asp Thr Asn His Thr Pro
                165                 170                 175

Val Ala Leu Tyr Pro Asp Ser Asp Leu Glu Lys Glu Glu Glu Ser
            180                 185                 190

Glu Glu Asp Trp Lys Leu Gln Leu Glu Ala Glu Asn Tyr Glu Gly His
        195                 200                 205

Thr Pro Leu His Val Ala Val Ile His Lys Asp Val Glu Met Val Arg
210                 215                 220

Leu Leu Arg Asp Ala Gly Ala Asp Leu Asp Lys Pro Glu Pro Thr Cys
225                 230                 235                 240

Gly Arg Ser Pro Leu His Leu Ala Val Glu Ala Gln Ala Ala Asp Val
                245                 250                 255

Leu Glu Leu Leu Leu Arg Ala Gly Ala Asn Pro Ala Ala Arg Met Tyr
            260                 265                 270

Gly Gly Arg Thr Pro Leu Gly Ser Ala Met Leu Arg Pro Asn Pro Ile
        275                 280                 285

Leu Ala Arg Leu Leu Arg Ala His Gly Ala Pro Glu Pro Glu Gly Glu
    290                 295                 300

Asp Glu Lys Ser Gly Pro Cys Ser Ser Ser Asp Ser Asp Ser Gly
305                 310                 315                 320

Asp Glu Gly Val Ser Gln Glu Glu Arg Gln Gly Ser Pro Ala Gly Gly
                325                 330                 335

Ser Gly

<210> SEQ ID NO 6
<211> LENGTH: 264
<212> TYPE: PRT
<213> ORGANISM: Homo sapiens

<400> SEQUENCE: 6

```
Met Ala Gly Val Ala Cys Leu Gly Lys Ala Asp Ala Asp Glu Trp
1               5                   10                  15

Cys Asp Ser Gly Leu Gly Ser Leu Gly Pro Asp Ala Ala Pro Gly
            20                  25                  30

Gly Pro Gly Leu Gly Ala Glu Leu Gly Pro Gly Leu Ser Trp Ala Pro
            35                  40                  45

Leu Val Phe Gly Tyr Val Thr Glu Asp Gly Asp Thr Ala Leu His Leu
    50                  55                  60

Ala Val Ile His Gln His Glu Pro Phe Leu Asp Phe Leu Leu Gly Phe
65                  70                  75                  80

Ser Ala Gly Thr Glu Tyr Met Asp Leu Gln Asn Asp Leu Gly Gln Glu
                85                  90                  95

Glu Glu Glu Ser Glu Glu Asp Trp Lys Leu Gln Leu Glu Ala Glu Asn
            100                 105                 110

Tyr Glu Gly His Thr Pro Leu His Val Ala Val Ile His Lys Asp Val
            115                 120                 125

Glu Met Val Arg Leu Leu Arg Asp Ala Gly Ala Asp Leu Asp Lys Pro
130                 135                 140

Glu Pro Thr Cys Gly Arg Ser Pro Leu His Leu Ala Val Glu Ala Gln
145                 150                 155                 160

Ala Ala Asp Val Leu Glu Leu Leu Leu Arg Ala Gly Ala Asn Pro Ala
                165                 170                 175

Ala Arg Met Tyr Gly Gly Arg Thr Pro Leu Gly Ser Ala Met Leu Arg
            180                 185                 190

Pro Asn Pro Ile Leu Ala Arg Leu Leu Arg Ala His Gly Ala Pro Glu
            195                 200                 205

Pro Glu Gly Glu Asp Glu Lys Ser Gly Pro Cys Ser Ser Ser Ser Asp
        210                 215                 220

Ser Asp Ser Gly Asp Glu Gly Asp Glu Tyr Asp Asp Ile Val Val His
225                 230                 235                 240

Ser Ser Arg Ser Gln Thr Arg Leu Pro Pro Thr Pro Ala Ser Lys Pro
                245                 250                 255

Leu Pro Asp Asp Pro Arg Pro Val
            260
```

<210> SEQ ID NO 7
<211> LENGTH: 500
<212> TYPE: PRT
<213> ORGANISM: Homo sapiens

<400> SEQUENCE: 7

```
Met Asn Gln Arg Arg Ser Glu Ser Arg Pro Gly Asn His Arg Leu Gln
1               5                   10                  15

Ala Tyr Ala Glu Pro Gly Lys Gly Asp Ser Gly Gly Ala Gly Pro Leu
            20                  25                  30

Ser Gly Ser Ala Arg Arg Gly Arg Gly Gly Gly Ala Ile Arg Val
            35                  40                  45

Arg Arg Pro Cys Trp Ser Gly Gly Ala Gly Arg Gly Gly Pro Ala
    50                  55                  60

Trp Ala Val Arg Leu Pro Thr Val Thr Ala Gly Trp Thr Trp Pro Ala
65                  70                  75                  80

Leu Arg Thr Leu Ser Ser Leu Arg Ala Gly Pro Ser Glu Pro His Ser
                85                  90                  95
```

```
Pro Gly Arg Arg Pro Arg Ala Gly Arg Pro Leu Cys Gln Ala Asp
            100                 105                 110
Pro Gln Pro Gly Lys Ala Ala Arg Arg Ser Leu Glu Pro Asp Pro Ala
            115                 120                 125
Gln Thr Gly Pro Arg Pro Ala Arg Ala Ala Gly Met Ser Glu Ala Arg
    130                 135                 140
Lys Gly Pro Asp Glu Ala Glu Glu Ser Gln Tyr Asp Ser Gly Ile Glu
145                 150                 155                 160
Ser Leu Arg Ser Leu Arg Ser Leu Pro Glu Ser Thr Ser Ala Pro Ala
                165                 170                 175
Ser Gly Pro Ser Asp Gly Ser Pro Gln Pro Cys Thr His Pro Pro Gly
            180                 185                 190
Pro Val Lys Glu Pro Gln Glu Lys Glu Asp Ala Asp Gly Glu Arg Ala
            195                 200                 205
Asp Ser Thr Tyr Gly Ser Ser Leu Thr Tyr Thr Leu Ser Leu Leu
    210                 215                 220
Gly Gly Pro Glu Ala Glu Asp Pro Ala Pro Arg Leu Pro Leu Pro His
225                 230                 235                 240
Val Gly Ala Leu Ser Pro Gln Gln Leu Glu Ala Leu Thr Tyr Ile Ser
                245                 250                 255
Glu Asp Gly Asp Thr Leu Val His Leu Ala Val Ile His Glu Ala Pro
            260                 265                 270
Ala Val Leu Leu Cys Cys Leu Ala Leu Leu Pro Gln Glu Val Leu Asp
            275                 280                 285
Ile Gln Asn Asn Leu Tyr Gln Thr Ala Leu His Leu Ala Val His Leu
            290                 295                 300
Asp Gln Pro Gly Ala Val Arg Ala Leu Val Leu Lys Gly Ala Ser Arg
305                 310                 315                 320
Ala Leu Gln Asp Arg His Gly Asp Thr Ala Leu His Val Ala Cys Gln
                325                 330                 335
Arg Gln His Leu Ala Cys Ala Arg Cys Leu Leu Glu Gly Arg Pro Glu
            340                 345                 350
Pro Gly Arg Gly Thr Ser His Ser Leu Asp Leu Gln Leu Gln Asn Trp
            355                 360                 365
Gln Gly Leu Ala Cys Leu His Ile Ala Thr Leu Gln Lys Asn Gln Pro
    370                 375                 380
Leu Met Glu Leu Leu Leu Arg Asn Gly Ala Asp Ile Asp Val Gln Glu
385                 390                 395                 400
Gly Thr Ser Gly Lys Thr Ala Leu His Leu Ala Val Glu Thr Gln Glu
                405                 410                 415
Arg Gly Leu Val Gln Phe Leu Leu Gln Ala Gly Ala Gln Val Asp Ala
            420                 425                 430
Arg Met Leu Asn Gly Cys Thr Pro Leu His Leu Ala Ala Gly Arg Gly
            435                 440                 445
Leu Met Gly Ile Ser Ser Thr Leu Cys Lys Ala Gly Ala Asp Ser Leu
    450                 455                 460
Leu Arg Asn Val Glu Asp Glu Thr Pro Gln Asp Leu Thr Glu Glu Ser
465                 470                 475                 480
Leu Val Leu Leu Pro Phe Asp Asp Leu Lys Ile Ser Gly Lys Leu Leu
                485                 490                 495
Leu Cys Thr Asp
            500
```

```
<210> SEQ ID NO 8
<211> LENGTH: 454
<212> TYPE: PRT
<213> ORGANISM: Homo sapiens

<400> SEQUENCE: 8

Met Pro Arg Cys Pro Ala Gly Ala Met Asp Glu Gly Pro Val Asp Leu
1               5                   10                  15

Arg Thr Arg Pro Lys Ala Ala Gly Leu Pro Gly Ala Ala Leu Pro Leu
            20                  25                  30

Arg Lys Arg Pro Leu Arg Ala Pro Ser Pro Glu Pro Ala Ala Pro Arg
        35                  40                  45

Gly Ala Ala Gly Leu Val Val Pro Leu Asp Pro Leu Arg Gly Gly Cys
    50                  55                  60

Asp Leu Pro Ala Val Pro Gly Pro Pro His Gly Leu Ala Arg Pro Glu
65                  70                  75                  80

Ala Leu Tyr Tyr Pro Gly Ala Leu Leu Pro Leu Tyr Pro Thr Arg Ala
                85                  90                  95

Met Gly Ser Pro Phe Pro Leu Val Asn Leu Pro Thr Pro Leu Tyr Pro
            100                 105                 110

Met Met Cys Pro Met Glu His Pro Leu Ser Ala Asp Ile Ala Met Ala
        115                 120                 125

Thr Arg Ala Asp Glu Asp Gly Asp Thr Pro Leu His Ile Ala Val Val
    130                 135                 140

Gln Gly Asn Leu Pro Ala Val His Arg Leu Val Asn Leu Phe Gln Gln
145                 150                 155                 160

Gly Gly Arg Glu Leu Asp Ile Tyr Asn Asn Leu Arg Gln Thr Pro Leu
                165                 170                 175

His Leu Ala Val Ile Thr Thr Leu Pro Ser Val Val Arg Leu Leu Val
            180                 185                 190

Thr Ala Gly Ala Ser Pro Met Ala Leu Asp Arg His Gly Gln Thr Ala
        195                 200                 205

Ala His Leu Ala Cys Glu His Arg Ser Pro Thr Cys Leu Arg Ala Leu
    210                 215                 220

Leu Asp Ser Ala Ala Pro Gly Thr Leu Asp Leu Glu Ala Arg Asn Tyr
225                 230                 235                 240

Asp Gly Leu Thr Ala Leu His Val Ala Val Asn Thr Glu Cys Gln Glu
                245                 250                 255

Thr Val Gln Leu Leu Leu Glu Arg Gly Ala Asp Ile Asp Ala Val Asp
            260                 265                 270

Ile Lys Ser Gly Arg Ser Pro Leu Ile His Ala Val Glu Asn Asn Ser
        275                 280                 285

Leu Ser Met Val Gln Leu Leu Leu Gln His Gly Ala Asn Val Asn Ala
    290                 295                 300

Gln Met Tyr Ser Gly Ser Ser Ala Leu His Ser Ala Ser Gly Arg Gly
305                 310                 315                 320

Leu Leu Pro Leu Val Arg Thr Leu Val Arg Ser Gly Ala Asp Ser Ser
                325                 330                 335

Leu Lys Asn Cys His Asn Asp Thr Pro Leu Met Val Ala Arg Ser Arg
            340                 345                 350

Arg Val Ile Asp Ile Leu Arg Gly Lys Ala Thr Arg Pro Ala Ser Thr
        355                 360                 365

Ser Gln Pro Asp Pro Ser Pro Asp Arg Ser Ala Asn Thr Ser Pro Glu
    370                 375                 380
```

```
Ser Ser Ser Arg Leu Ser Ser Asn Gly Leu Leu Ser Ala Ser Pro Ser
385                 390                 395                 400

Ser Ser Pro Ser Gln Ser Pro Pro Arg Asp Pro Pro Gly Phe Pro Met
            405                 410                 415

Ala Pro Pro Asn Phe Phe Leu Pro Ser Pro Ser Pro Ala Phe Leu
            420                 425                 430

Pro Phe Ala Gly Val Leu Arg Gly Pro Gly Arg Pro Val Pro Pro Ser
        435                 440                 445

Pro Ala Pro Gly Gly Ser
    450
```